United States Patent
Yue et al.

(10) Patent No.: US 11,795,197 B2
(45) Date of Patent: Oct. 24, 2023

(54) PEPTIDE COMPOSITIONS FOR IMMUNO-ONCOLOGY MOLECULAR IMAGING AND TARGETED DRUG DELIVERY

(71) Applicant: Cedars-Sinai Medical Center, Los Angeles, CA (US)

(72) Inventors: Yong Yue, Los Angeles, CA (US); Yi Zhang, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 368 days.

(21) Appl. No.: 16/616,692

(22) PCT Filed: Jun. 7, 2018

(86) PCT No.: PCT/US2018/036479
§ 371 (c)(1),
(2) Date: Nov. 25, 2019

(87) PCT Pub. No.: WO2018/226971
PCT Pub. Date: Dec. 13, 2018

(65) Prior Publication Data
US 2021/0284689 A1 Sep. 16, 2021

Related U.S. Application Data

(60) Provisional application No. 62/516,598, filed on Jun. 7, 2017.

(51) Int. Cl.
| | | |
|---|---|---|
| *C07K 7/06* | (2006.01) | |
| *A61K 45/06* | (2006.01) | |
| *A61K 49/00* | (2006.01) | |
| *A61K 49/14* | (2006.01) | |
| *A61K 51/08* | (2006.01) | |
| *G01N 33/574* | (2006.01) | |
| *A61K 38/00* | (2006.01) | |

(52) U.S. Cl.
CPC ............... *C07K 7/06* (2013.01); *A61K 45/06* (2013.01); *A61K 49/0002* (2013.01); *A61K 49/0056* (2013.01); *A61K 49/14* (2013.01); *A61K 51/088* (2013.01); *G01N 33/57484* (2013.01); *A61K 38/00* (2013.01)

(58) Field of Classification Search
CPC ...... A61K 51/087; A61K 38/08; A61K 38/00; A61K 38/03; C07K 7/06
See application file for complete search history.

(56) References Cited

U.S. PATENT DOCUMENTS

| | | |
|---|---|---|
| 2003/0009022 A1 | 1/2003 | Klein et al. |
| 2003/0186852 A1 | 3/2003 | Heins et al. |
| 2011/0044893 A1 | 2/2011 | Schnitzer et al. |
| 2012/0093723 A1 | 4/2012 | Sinko et al. |
| 2013/0196332 A1 | 8/2013 | Morris et al. |
| 2015/0050213 A1 * | 2/2015 | Stone ................... A61K 51/088 424/1.69 |
| 2016/0220692 A1 | 8/2016 | Pienta |

FOREIGN PATENT DOCUMENTS

| | | | |
|---|---|---|---|
| WO | WO-2009044279 A2 * | 4/2009 | ............. C07K 11/02 |
| WO | 2018226971 A1 | 12/2018 | |

OTHER PUBLICATIONS

Vital et al. "Formyl-Peptide Receptor 1/3/Lipoxin A4 Receptor Regulates Neutrophil-Platelet Aggregation and Attenuates Cerebral Inflammation", Circulation, 2016, pp. 2169-2179 (Year: 2016).*
Kastin "Handbook of Biologically Active Peptides", 2013, Academic Press, pp. 667-668 (Year: 2013).*
Ajmone-Cat et al. "Non-Steroidal Anti-Inflammatory Drugs and Brain Inflammation: Effects on Microglial Functions", Pharmaceuticals, 2010, pp. 1949-1964 (Year: 2010).*
Li et al. "Multimodal formyl peptide receptor 1 targets inflammation imaging probe: cFLFLF-MHI-DOTA", Bioorganic and Medicinal Chemistry Letters, published online Dec. 12, 2015, pp. 1052-1055 (Year: 2015).*
International Search Report and Written Opinion of PCT/US2018/036479, dated Sep. 17, 2018, 11 Pages.
Kastin, Abba, Handbook of Biologically Active Peptides, 2013, Academic Press, p. 667, col. 2, Second Paragraph, 3 Pages.

* cited by examiner

*Primary Examiner* — Lianko G Garyu
(74) *Attorney, Agent, or Firm* — Nixon Peabody LLP

(57) ABSTRACT

Described herein is a peptide, a multimodal peptide ligand imaging agent and methods for use in tumor targeting, tumor visualization, drug delivery and as an imaging ligand. The invention further provides for a theranostic peptide agent and methods for use in the treatment of cancer and/or inflammation in a subject.

20 Claims, 9 Drawing Sheets
Specification includes a Sequence Listing.

US 11,795,197 B2

PEPTIDE COMPOSITIONS FOR IMMUNO-ONCOLOGY MOLECULAR IMAGING AND TARGETED DRUG DELIVERY

CROSS-REFERENCE TO RELATED APPLICATIONS

This application is a National Phase of International Application No. PCT/US2018/036479 filed Jun. 7, 2018, which designated the U.S. and that International Application was published under PCT Article 21(2) in English, which also includes a claim of priority under 35 U.S.C. § 119(e) to U.S. provisional patent application No. 62/516,598 filed Jun. 7, 2017, the entirety of which is hereby incorporated by reference.

FIELD OF THE INVENTION

This invention relates to peptide compositions and methods for use in tumor targeting, tumor visualization, drug delivery, as an imaging ligand and treatment of cancer and/or inflammation.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Clinical evidence shows that high levels of tumor-associated immuno-activities (e.g. inflammation, neutrophils and macrophages) in tumor tissues correlate with poor prognosis of cancer. Currently, no effective clinical screen strategy is available to detect cancer at early stage and select individual patients for targeted treatment, and no effective method is available to improve the efficacy of treatment of cancer patients.

To improve patient survival, two important aspects of cancer patient management need to be addressed: early diagnosis and monitoring disease progression during and post treatment. Current available clinical approaches, including imaging and immunochemistry (IHC), have their limitations in fulfilling these requirements. Clinical diagnostic imaging approaches typically are not associated with tumor specific targets and have difficulty correlating with tumorigenesis, progression and migration functions.

Evaluation of IHC biomarkers can only occur after invasive procedures, e.g. biopsy or surgery, limiting the timeliness and usefulness of this evaluation method. The availability of a tumor-specific, molecular-genetic imaging approach which integrates evaluation of cancer microenvironment biology and global tumor morphological characteristics without invasive surgical procedures would be highly desirable for both early diagnosis and the monitoring of disease progression during and post treatment.

Therefore, there is a need in the art for the identification of a multimodal peptide imaging agent for use in tumor targeting, tumor visualization, drug delivery and as an imaging ligand and a theranostic agent comprising the multimodal peptide imaging agent for use in treating cancer and/or inflammation in a subject.

SUMMARY OF THE INVENTION

The following embodiments and aspects thereof are described and illustrated in conjunction with compositions and methods which are meant to be exemplary and illustrative, not limiting in scope.

Various embodiments of the present invention provide for a peptide comprising the sequence as set forth in SEQ ID NO:1. In various embodiments, the peptide consist of the sequence as set forth in SEQ ID:1. In other embodiments, the peptide consist of the sequence as set forth in SEQ ID NO:1 and a linker.

Various embodiments of the present invention provide for a multimodal peptide ligand imaging agent, comprising: a peptide ligand capable of selectively binding to formyl peptide receptors (FPRs); an imaging moiety; and optionally, a linker that binds the peptide ligand and imaging moiety.

In various embodiments, the multimodal peptide ligand imaging agent can comprise the linker that binds the peptide ligand and imaging moiety.

In various embodiments, the FPR can be formyl peptide receptor 1 (FPR1).

In various embodiments, the peptide ligand can comprise SEQ ID NO:1.

In various embodiments, the imaging moiety can be a nuclear imaging radioisotope, a magnetic resonance imaging (MRI) imaging probe, or optical imaging fluorophore.

In various embodiments, the linker can be a lysine linker or a PEG linker.

Various embodiments of the present invention provide for a theranostic peptide agent, comprising: a multimodal peptide ligand imaging agent of the present invention; a therapeutic agent; and optionally, a linker that binds the multimodal peptide ligand imaging agent and the therapeutic agent.

In various embodiments, theranostic peptide agent can comprise the linker that binds the multimodal peptide ligand imaging agent and the therapeutic agent.

In various embodiments, the FPR of the multimodal peptide ligand imaging agent can be formyl peptide receptor 1 (FPR1).

In various embodiments, the peptide ligand of the multimodal peptide ligand imaging agent can comprise SEQ ID NO:1.

In various embodiments, the imaging moiety of the multimodal peptide ligand imaging agent can be a nuclear imaging radioisotope, a magnetic resonance imaging (MRI) imaging probe, or optical imaging fluorophore.

In various embodiments, the linker that binds the peptide ligand and imaging moiety can be a lysine linker or a PEG linker, and the linker that binds the multimodal peptide ligand imaging agent and the therapeutic agent can also be a lysine linker or a PEG linger.

In various embodiments, the therapeutic agent can be a cancer therapeutic and/or an anti-inflammatory agent. In various embodiments, the therapeutic agent can be covalently conjugated with the peptide ligand of the multimodal peptide ligand imaging agent.

Various embodiments of the present invention provide for a method, comprising: administering the multimodal peptide ligand imaging agent of the present invention to a subject in need thereof; assessing the subject by imaging and detecting the multimodal peptide ligand imaging agent; and diagnosing the subject with cancer and/or inflammation when the multimodal peptide ligand imaging agent is detected.

In various embodiments, the imaging moiety of the multimodal peptide ligand imaging agent can detect targeted tissues and/or cells.

In various embodiments, the targeted tissues and/or cells can comprise tumor and/or inflammatory regions. In various embodiments, the targeted tissues and/or cells can comprise immune-associated tumor cells.

In various embodiments, the method can further comprise visualizing the targeted tissues and/or cells using imaging methods. In various embodiments, the method can further comprise prognosticating cancer and/or inflammation in the subject using a multimodal peptide ligand imaging agent of the present invention. In various embodiments, prognosticating cancer and/or inflammation can comprise detecting the location and extent of the tumor region and/or the inflammatory region by detecting levels of the imaging moiety.

In various embodiments, higher levels of the imaging moiety detected can be indicative of a bad prognosis and lower levels of the imaging moiety detected is indicative of a good prognosis.

In various embodiments, the method can further comprise staging the cancer and/or inflammation in the subject using the multimodal peptide ligand imaging agent of the present invention. In various embodiments, the method can further comprise clinically screening patients for targeted treatment using the multimodal peptide ligand imaging agent.

Various embodiments of the invention provide for a method, comprising: administering a theranostic peptide agent of the present invention to a subject with cancer and/or inflammation to treat the subject.

In various embodiments, the subject can have cancer. In various embodiments, the cancer can be an Annexin 1 (ANXA1)-expressing cancer. In various embodiments, the cancer can be a formyl peptide receptor 1 (FPR1) expressing cancer.

In various embodiments, the method can further comprise identifying targeted tissues and/or cells by detecting the imaging moiety of the multimodal peptide ligand imaging agent.

In various embodiments, the targeted tissues and/or cells can comprise tumor and/or inflammatory regions. In various embodiments, the targeted tissues and/or cells can comprise immune-associated tumor cells.

In various embodiments, the method can further comprise visualizing the targeted tissue/cells using imaging methods.

In various embodiments, the therapeutic agent of the theranostic peptide agent can be a cancer therapeutic. In various embodiments, the therapeutic agent of the theranostic peptide agent can be an anti-inflammatory agent.

In various embodiments, the method can further comprise monitoring the therapeutic response by detecting the imaging moiety of the multimodal peptide ligand imaging agent. In various embodiments, the method can further comprise monitoring the targeted tissues and/or cells. In various embodiments, the method can further comprise comprising monitoring infiltration of tumor-associated macrophages and neutrophils.

BRIEF DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION

Figure 1:
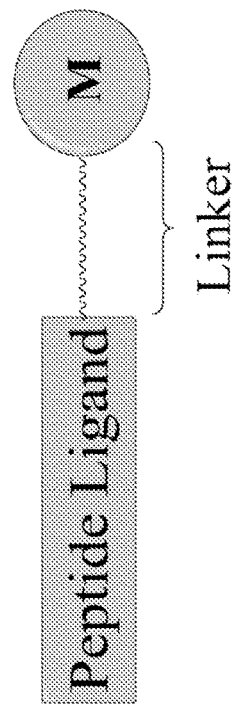
FIG. 1 depicts in accordance with various embodiments of the invention, a multimodal peptide imaging agent. The imaging probe can be used for multimodal imaging by conjugating the peptide with imaging moieties.

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* $22^{nd}$ ed, Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* $3^{rd}$ ed, revised ed., J. Wiley & Sons (New York, N.Y. 2006); Smith, *March's Advanced Organic Chemistry Reactions, Mechanisms and Structure* $7^{th}$ ed., J. Wiley & Sons (New York, N.Y. 2013); Singleton, *Dictionary of DNA and Genome Technology* $3^{rd}$ ed., Wiley-Blackwell (Nov. 28, 2012); and Green and Sambrook, *Molecular Cloning: A Laboratory Manual* 4th ed, Cold Spring Harbor Laboratory Press (Cold Spring Harbor, N.Y. 2012), provide one skilled in the art with a general guide to many of the terms used in the present application. For references on how to prepare antibodies, see Greenfield, Antibodies *A Laboratory Manual* $2^{nd}$ ed., Cold Spring Harbor Press (Cold Spring Harbor N.Y., 2013); Köhler and Milstein, Derivation of specific antibody-producing tissue culture and tumor lines by cell fusion, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For purposes of the present invention, the following terms are defined below.

Terms such as "treating" or "treatment" or "to treat" or "alleviating" or "to alleviate" refer to therapeutic treatment and/or prophylactic or preventative measures, wherein the object is to prevent or slow down (lessen) the pathologic condition, prevent the pathologic condition, pursue or obtain good overall survival, or lower the chances of the individual developing the condition even if the treatment is ultimately unsuccessful. Thus, those in need of treatment include those already with the disorder; those prone to have the disorder; and those in whom the disorder is to be prevented.

The term "therapeutically effective amount" refers to an amount of a therapeutic agent effective to "treat" a disease or disorder in a subject. In various embodiments, the therapeutic agent is conjugated to the multimodal peptide imaging agent.

The term "subject" refers to any animal (e.g., a mammal), including, but not limited to humans, non-human primates, rodents, and domestic and game animals, which is to be the recipient of a particular treatment. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Typically, the terms "subject" and "patient" are used interchangeably herein in reference to a human subject. In various embodiments, a subject can be one who has been previously diagnosed with or identified as suffering from or having a condition in need of treatment. In various other embodiments, the subject previously diagnosed with or identified as suffering from or having a condition may or may not have undergone treatment for a condition. In yet other embodiments, a subject can also be one who has not been previously diagnosed as having a condition (i.e., a subject who exhibits one or more risk factors for a condition). A "subject in need" of treatment for a particular condition can be a subject having that condition, diagnosed as having that condition, or at risk of developing that condition.

The terms "cancer" and "cancerous" refer to or describe the physiological condition in mammals that is typically characterized by unregulated cell growth. Included in this definition are malignant cancers as well as dormant tumors or micrometastatses. Examples of cancer include, but are not limited to, breast, brain, lung, pancreatic, kidney, stomach, uterine, cervical, colorectal, bladder, skin and/or head and neck cancer. The cancer may be newly diagnosed, diagnosed, or recurrent.

"Tumor," as used herein refers to all neoplastic cell growth and proliferation, whether malignant or benign, and all pre-cancerous and cancerous cells and tissues.

Breast cancer is a heterogeneous disease with a wide array of clinical, imaging, pathological, and molecular features. Triple negative breast carcinomas (TNBC), defined by the lack of expression of three common molecular markers ER, PR and HER2, clinically presents with larger tumor size, higher grade, increased number of involved lymph nodes, and poorer overall survival compared with other breast cancers. What makes this disease more aggressive is that TNBC tends to be rapidly progressive and quickly develops symptomatic metastases. To improve patient survival, two important aspects of TNBC patient management need to be addressed: early diagnosis and monitoring disease progression during and post treatment.

Current available clinical approaches, including imaging and immunochemistry (IHC), have their limitations in fulfilling these requirements. Clinical diagnostic imaging approaches typically are not associated with tumor specific targets and have difficulty correlating with tumorigenesis, progression and migration functions.

Evaluation of IHC biomarkers can only occur after invasive procedures, e.g. biopsy or surgery, limiting the timeliness and usefulness of this evaluation method. The availability of a tumor-specific molecular-genetic imaging approach which integrates evaluation of breast cancer microenvironment biology and global tumor morphological characteristics without invasive surgical procedures would be highly desirable for both early diagnosis and the monitoring of disease progression during and post treatment.

Annexin A1 (ANXA1) is a calcium- and phospholipid-binding protein and is considered to play an important role in tumorigenesis. Recent studies have shown ANXA1 is highly expressed in certain phenotype of cancer (e.g. breast cancer, pancreatic cancer), and functionally involved in regulation of tumorigenesis, progression and metastasis formation in multiple cancer. This allows ANXA1 to be an excellent biomarker candidate for diagnosis and monitoring tumor functions. However, direct tracking of ANXA1 biology functions is difficult since it requires an externalization process which enables the ANXA1 protein to interact with specific binding sites outside cell membranes. Its cognate partners, FPRs, which are the only known receptors with externalized ANXA1, play an important role in AXNA1 regulated proliferation and migration. Therefore, the invention looks to FPR as a surrogate for monitoring ANXA1 behavior in cancer.

In addition to its association with cancer, the formyl peptide receptors (FPR) belong to a class of G protein-coupled receptors involved in chemotaxis. These receptors have the ability to bind N-formyl peptides such as N-formylmethionine produced by the degradation of either bacterial or host cells. Hence, formyl peptide receptors are involved in mediating immune cell response to infection and may act to suppress the immune system under certain conditions. In humans, there are three formyl peptide receptor isoforms, FPR1, FPR2, and FPR3.

As described herein, the inventors discuss the use of a novel molecular imaging strategy involving a FPR1 specific binding peptide, LDLLDL (SEQ ID NO:1), conjugated with an imaging moiety and/or a therapeutic agent. The FPR specific small molecule LDLLDL (SEQ ID NO:1) targets ANXA1-expressing breast carcinomas allowing non-specific imaging radioisotope to accumulate in the tumor region. Linking $^{64}$Cu to LDLLDL (SEQ ID NO:1) ensures temporal and spatial delivery of the imaging probe to the tumor region so that systemic imaging of LDLLDL-$^{64}$Cu ([SEQ ID NO:1]-$^{64}$Cu) can be used effectively to monitor tumorigenesis, migration and metastasis of TNBC.

This invention is designed to use the peptidomimetic sequence LDLLDL (SEQ ID NO:1) to target the tumor's N-Formyl peptide receptor 1 (FPR 1), which is abundantly expressed on the surface of inflammation related cells and tumor cells. With the tagging of imaging moieties, the peptide agent will be used to detect immune-associated tumor cells, and monitor the infiltration of tumor-associated macrophages and neutrophils. In conjunction with a therapeutic drug, the agent will be used for targeted drug delivery in pre-clinical in vitro/in vivo studies and clinical trials in patients.

Recent efforts have been devoted to the creation of targeting agents that accumulate at sites of interest and emit a signal that can be detected by imaging scanner, e.g. positron emission tomography (PET), MRI. The inventors have shown that another peptide (cFlFIF) can be used to detect acute inflammation due to trauma, infection in pancreas, brain and other non-cancer disease (Zhang et al. Bioorg. Med. Chem. Lett. 2007 17(24):6876-6878). Although the cFlFIF shows promise for in vivo detection of inflammation in experimental models, several problems remain. The peptide cFlFIF is highly hydrophobic and needs to be PEGylated with a large polyethylene glycol (PEG) to improve its solubility. In addition, cFlFIF demonstrates low uptake in tumor regions due to the low receptor affinity, which leads to non-specific targeting for tumor diagnosis and treatment.

The inventors have successfully synthesized an FPR 1 peptide (LDLLDL, SEQ ID NO:1) and its cyanine 7 (cy7) derivative. Cellular uptake and animal studies show that the peptide-cy7 conjugates internalized into the cancer cells and their near infrared fluorescence can be visualized by fluorescence microscopy and fluorescence animal imaging. The FPR 1 antagonist peptide that has the properties of fast binding to, but not activating the receptor, is an attractive agent for the imaging probes to detect inflammation and tumor regions.

As described herein, using a hexapeptide antagonist, Leu-Asp-Leu-Leu-Asp-Leu (LDLLDL, SEQ ID NO:1), the inventors describe novel compositions and their synthesis for tumor targeting, tumor visualization, drug delivery and use as an imaging ligand. The peptide ligand is also used in a theranostic agent for the diagnosis and therapy of cancer and inflammation. The imaging moieties and drug payloads are conjugated with the peptidomimetic sequence LDLLDL (SEQ ID NO:1) through linkers and chelators. LDLLDL (SEQ ID NO:1) selectively binds with formyl peptide receptor 1 (FPR1) which is expressed on the activated immune cells and cancer cells, and therefore reveals the location and extent of the tumor region using imaging modalities (optical, SPECT, PET, MRI, etc.). In addition, the peptide ligand can carry the therapeutic drug to cancer cells to achieve targeted delivery. The peptide ligand can be used for diagnosis, staging, prognosis, treatment, and monitoring therapeutic response of a variety of cancer treatment interventions, among other things.

The present invention is based, at least in part, on these findings. Embodiments address the need in the art for a multimodal peptide ligand imaging agent and methods for use in tumor targeting, tumor visualization, drug delivery and as an imaging ligand. Embodiments further provide for a theranostic imaging agent and methods of use for the treatment of cancer and/or inflammation in a subject.

Peptide

Various embodiments provide for a peptide comprising the following sequence Leu-Asp-Leu-Leu-Asp-Leu (SEQ ID NO:1).

In various embodiments, the peptide consists of the sequence as set forth in SEQ ID:1. In various embodiments, the peptide consists of the sequence as set forth in SEQ ID NO:1 and a linker. In various embodiments, the linker is a lysine linker or a PEG linker. In various embodiments, the linker is as further described herein.

Multimodal Peptide Ligand Imaging Agent and Theranostic Peptide Agent

The multimodal peptide ligand imaging agent of the invention is useful in a variety of applications including, but not limited to, diagnosing, staging, prognosing of cancer and/or inflammation and the monitoring of a therapeutic response. In various embodiments, the multimodal peptide ligand imaging agent is used in tumor targeting, tumor visualization and/or as an imaging ligand.

The theranostic peptide agent of the invention, which comprises the multimodal peptide ligand imaging agent and a therapeutic agent, is useful in a variety of applications including, but not limited to, therapeutic treatment methods, such as the treatment of cancer and/or inflammation. In various embodiments, the theranostic peptide agent is used for drug delivery. In various other embodiments, the theranostic peptide agent specifically targets the area of treatment and drug delivery.

In various embodiments, the multimodal peptide ligand imaging agent or the theranostic peptide agent can be used in vitro, ex vivo, or in vivo.

Various embodiments of the present invention provide for a multimodal peptide ligand imaging agent, comprising: a peptide ligand capable of selectively binding to formyl peptide receptors (FPRs); an imaging moiety, and a linker that binds the peptide ligand and imaging moiety.

In various embodiments, the peptide ligand comprises SEQ ID NO: 1.

In various embodiments, the FPR is formyl peptide receptor 1 (FPR1).

In various embodiments, the imaging moiety is a nuclear imaging radioisotope, a magnetic resonance imaging (MRI) imaging probe, or optical imaging fluorophore.

In various embodiments, the linker is a lysine linker or a PEG linker. In various embodiments, the linker is as further described herein.

Various embodiments of the present invention provide for a theranostic peptide agent, comprising: a multimodal peptide ligand imaging agent of the present invention; a therapeutic agent; and a linker that binds the multimodal peptide ligand imaging agent and the therapeutic agent.

In various embodiments, the peptide ligand comprises SEQ ID NO: 1.

In various embodiments, the FPR is formyl peptide receptor 1 (FPR1).

In various embodiments, the imaging moiety is a nuclear imaging radioisotope, a magnetic resonance imaging (MRI) imaging probe, or optical imaging fluorophore.

In various embodiments, the linker is a lysine linker or a PEG linker. In various embodiments, the linker is as further described herein.

In various embodiments, the therapeutic agent is a cancer therapeutic and/or an anti-inflammatory agent. In various other embodiments, the therapeutic agent is covalently conjugated with the peptide ligand of the multimodal peptide ligand imaging agent. In other embodiments, the therapeutic agent is covalently conjugated with the peptide ligand of the multimodal peptide ligand imaging agent through an amide bond.

In various embodiments of the invention, the cancer therapeutic is a chemotherapy drug. Examples of a cancer therapeutic include, but are not limited to, Platinum agents (cisplatin, carboplatin), Bevacizumab, Docetaxel, Camptothecin, Chlorin E6, Oxaliplatin, Carmustine, Cyclophosphamide, Vincristine, Ixabepilone, Eribulin, Vinorelbine, Vinblastine, Irinotecan, Topotecan, Etoposide, Paclitaxel, Doxorubicin, Lomustine, Everolimus, Temozolomide, Taxotere, Pemetrexed, Cabazitaxel, Estramustine, Capecitabine, Gemcitabine, and Mitoxantrone.

In various other embodiments, the therapeutic agent is an anti-inflammatory drug. In some embodiments, the anti-inflammatory drug is a non-steroidal anti-inflammatory drug. In various other embodiments, the anti-inflammatory drug is an immune selective anti-inflammatory derivative. Examples of anti-inflammatory drugs include, but are not limited to, Aspirin, Ibuprofen, Paracetamol, Acetaminophen, Diclofenac, Naproxen, Meloxicam, Indomethacin, Metamizole, Celecoxib, Ketorolac, Ketoprofen, Piroxicam, Nimesulide, Etoricoxib, Mefenamic acid, Carprofen, Etodolac, Nabumetone, Flurbiprofen, Loxoprofen, Phenylbutazone, Sulindac, Aceclofenac, Dexketoprofen, Diflunisal, Benzydamine, Valdecoxib, Lornoxicam, Tenoxicam, Oxaprozin, Flunixin, Deracoxib, Fenoprofen, Tolmetin, Ethenzamide, Phenazone, Dexibuprofen, Lumiracoxib, Nepafenac, Bromfenac, and Fenbufen.

Various embodiments of the invention provide for a multimodal peptide ligand imaging agent comprising a peptide ligand conjugated to an imaging moiety.

Various other embodiments of the invention provide for a theranostic peptide agent comprising of the multimodal peptide ligand imaging agent and a therapeutic agent. The peptide ligand comprises of a sequence with six amino acids (SEQ ID NO: 1). In various embodiments, the imaging moiety can be conjugated to any one of the six amino acids. In various other embodiments, the therapeutic agent can be conjugated to any one of the six amino acids. In various embodiments, the imaging moiety and the therapeutic agent are conjugated at opposite ends of the peptide ligand. In various other embodiments, the imaging moiety and the therapeutic agent are conjugated opposite each other. In yet other embodiments, the imaging moiety and the therapeutic agent are conjugated next to each other.

Methods of Synthesis

Various embodiments of the present invention provide for the synthesis of the multimodal peptide ligand imaging agent and/or the theranostic peptide agent. Various methods of peptide synthesis are known and can be performed by one of skill in the art. Peptide synthesis methods include, but are not limited to, liquid phase synthesis and solid phase synthesis. In various embodiments, the peptide synthesis involves a solid support to assemble the peptide. Examples of a solid support include, but are not limited to, polystyrene resin, polyamide resin and/or PEG-based resin. In various other embodiments, the peptide synthesis involves a protecting group to synthesize the peptide. Examples of protecting groups include, but are not limited to, C-terminal protecting groups, N-terminal protecting groups (such as t-Boc and Fmoc protecting groups, Tert-butyloxycarbonyl (t-Boc) protection, 9H-fluoren-9-ylmethoxycarbonyl (Fmoc) protection), Benzyloxy-carbonyl, and side chain protecting groups. In various embodiments, the peptide ligand is synthesized using the solid-phase method. In various other embodiments, the peptide ligand is assembled on a resin. In yet other embodiments, the imaging probe of the multimodal peptide ligand imaging agent and/or the therapeutic agent of the theranostic peptide agent are covalently conjugated with the peptide ligand. In other embodiments, the imaging probe of the multimodal peptide ligand imaging agent and/or the therapeutic agent of the theranostic peptide agent are covalently conjugated with the peptide ligand. In various other embodiments, the imaging moiety and/or the therapeutic agent are conjugated with the w-group of the linker. In various embodiments, the linker is a lysine linker. In various embodiments, the linker is as further described herein.

Methods of Diagnosis and Detection

Various embodiments of the invention provide for a method, comprising: administering the multimodal peptide ligand imaging agent to a subject in need thereof; and detecting the multimodal peptide ligand imaging agent.

Various embodiments of the invention provide for a method, comprising: administering the multimodal peptide ligand imaging agent to a subject in need thereof; and detecting an accumulation of the multimodal peptide ligand imaging agent, as compared to normal cells or tissue. In various embodiments, the method further comprises calculating the concentration of the multimodal peptide ligand imaging agent. Calculation can be made; for example, based on a comparison control values.

Various embodiments of the invention provide for a method, comprising: administering the multimodal peptide ligand imaging agent to a subject in need thereof; and detecting an accumulation of the multimodal peptide ligand imaging agent, as compared to normal cells or tissue.

Various embodiments of the invention provide for a method, comprising: administering the multimodal peptide ligand imaging agent to a subject in need thereof; assessing the subject by imaging and detecting the multimodal peptide ligand imaging agent; and diagnosing the subject with cancer and/or an inflammation when the multimodal peptide ligand imaging agent is detected.

Various embodiments of the invention provide for a method, comprising: administering the multimodal peptide ligand imaging agent to a subject in need thereof; assessing the subject by imaging and detecting the multimodal peptide ligand imaging agent; and diagnosing the subject with cancer and/or an inflammation when an accumulation of multimodal peptide ligand imaging agent is detected as compared to normal cells or tissue.

In various embodiments, the imaging moiety of the multimodal peptide ligand imaging agent detects targeted tissues and/or cells. In various other embodiments, the targeted tissues and/or cells comprise tumor and/or inflammatory regions. In yet other embodiments, the targeted tissues and/or cells comprise immune-associated tumor cells.

In various embodiments, the method further comprises visualizing the targeted tissues and/or cells using imaging methods.

In various other embodiments, the method further comprises prognosticating cancer and/or an inflammation in the subject using the multimodal peptide ligand imaging agent. In various embodiments, prognosticating cancer and/or an inflammation comprises detecting the location and extent of the tumor region and/or the inflammatory region by detecting the levels of the imaging moiety. In various embodiments, a subject is prognosticated with cancer and/or inflammation when higher levels of the imaging moiety are detected. In various embodiments, a subject is not prognosticated with cancer and/or inflammation when lower levels of the imaging moiety are detected. In various embodiments, the levels of the imaging moiety are compared to a reference level. In various other embodiments, reference levels are obtained from normal subjects without cancer and/or inflammation and/or subjects who have been treated for cancer and/or inflammation.

In various embodiments, the method further comprises staging the cancer and/or inflammation in the subject using the multimodal peptide ligand imaging agent. The clinical stage of cancer is characterized by the TNM staging system described in the AJCC Cancer Staging Manual. For the tumor (T) stage, primary tumors with higher T stage (>2) will have higher levels of uptake (e.g., >5 nMol) of the imaging moiety, whereas low T (<2) stage will have less uptake of the imaging moiety (e.g., 0.5-5 nMol). Without being bound to any particular theory, it is expected that the imaging moiety can be detected at the early stage of tumor. For the nodal (N) stage, high levels of uptake of the imaging moiety in the locoregional lymph node will help identify those nodes which are invaded by cancer cells. The number of lymph nodes with detectable uptakes of the imaging moiety will help confirm pathological nodal stages. For the metastasis (M) stage, high level of uptake of the imaging moiety in the distance sites (other than primary site) will help identify the metastatic development of patients.

In various embodiments, the method further comprises clinically screening patients for targeted treatment using the multimodal peptide ligand imaging agent. Subjects with undetermined and/or ambiguous results from other screen approaches, can use the imaging moiety to evaluate the subject's condition and/or evaluate prior results, and provide accurate diagnosis for high-risk patients. The method can also be optimally implemented with other routine cancer screening approaches, e.g. MRI and nuclear imaging, by adjusting screening intervals. For asymptomatic individuals, routine screening using the imaging moiety may not be needed, but can be done.

In yet other embodiments, the method further comprises imaging the subject once or in a series of images following administration of the multimodal peptide ligand imaging agent.

In various embodiments, the subjects who have been diagnosed, prognosed, whose stage of cancer has been determined and/or who have been clinically screened for treatment, can be administered a conventional treatment known to one of skill in the art and/or the theranostic peptide agent described herein. In various other embodiments, the peptide compositions are administered to monitor treatment progress.

In various other embodiments, the multimodal peptide ligand imaging agent is administered prior to, simultaneously as or subsequent to treatment with conventional cancer and/or anti-inflammatory drugs. In certain embodiments, the multimodal peptide ligand imaging agent will be administered within 1 year of treatment with conventional cancer and/or anti-inflammatory drugs. In certain alternative embodiments, the multimodal peptide ligand imaging agent will be administered within 10, 8, 6, 4, or 2 months of treatment with conventional cancer and/or anti-inflammatory drugs. In certain other embodiments, the multimodal peptide ligand imaging agent will be administered within 4, 3, 2, or 1 week of treatment with conventional cancer and/or anti-inflammatory drugs. In some embodiments, the multimodal peptide ligand imaging agent will be administered within 5, 4, 3, 2, or 1 days of treatment with conventional cancer and/or anti-inflammatory drugs.

Methods of Treatment

Various embodiments of the present invention provide for a method, comprising: administering a theranostic peptide agent of the present invention to a subject with cancer to treat the subject.

Various embodiments of the present invention provide for a method, comprising: administering a theranostic peptide agent of the present invention to a subject with inflammation to treat the subject.

In certain embodiments, the theranostic peptide agents of the present invention are administered for the delivery of a drug for treatment. In various embodiments, the theranostic peptide agents of the present invention are administered to visualize the treatment area. In various other embodiments, the theranostic peptide agents of the present invention are administered to monitor treatment progress.

In various embodiments, the method further comprises identifying targeted tissues and/or cells by detecting the imaging moiety of the multimodal peptide ligand imaging agent. In various other embodiments, the targeted tissues and/or cells comprise tumor and/or inflammatory regions. In yet other embodiments, the targeted tissues and/or cells comprise immune-associated tumor cells. In various embodiments the method further comprises visualizing the targeted tissue/cells using imaging methods. In various other embodiments, the targeted tissues and/or cells are visualized prior to, simultaneously or subsequent to the administration of a therapeutic agent using the multimodal peptide ligand imaging agent.

In various embodiments, the therapeutic agent of the theranostic peptide agent is a cancer therapeutic and/or an anti-inflammatory. In various other embodiments, the therapeutic agent is a targeted drug that elicits a therapeutic response.

In yet other embodiments, the method further comprises monitoring the therapeutic response by detecting the imaging moiety of the multimodal peptide ligand imaging agent. In various embodiments, the method further comprises monitoring the targeted tissues and/or cells. In yet other embodiments, the method further comprises monitoring infiltration of tumor-associated macrophages and neutrophils.

In various embodiments, the administration of the theranostic peptide agent is therapeutic. In some embodiments, the administration of the theranostic peptide agent is therapeutic due to the targeting of specific cell populations. In other embodiments, the administration of the theranostic peptide agent is therapeutic due to the targeting of cancer cells. In other embodiments, the administration of the theranostic peptide agent is therapeutic due to the targeting of immune cells. In other embodiments, the administration of the theranostic peptide agent provides a prophylactic or preventative benefit.

In various other embodiments, the theranostic peptide agent is administered in a series of treatments. In some embodiments, the theranostic peptide agent and a second conventional cancer and/or anti-inflammatory treatment are administered in any order or concurrently.

It will further be appreciated that the two treatments may be administered to the subject within a matter of hours or minutes (i.e., simultaneously). In selected embodiments, the theranostic peptide agent will be administered to patients that have previously undergone treatment with a conventional cancer and/or anti-inflammatory treatment.

Conventional cancer and/or anti-inflammatory treatments include, but are not limited to those disclosed above. Other examples of conventional cancer treatments include, but are not limited to surgery, radiation therapy, chemotherapy, immunotherapy, targeted therapy, hormone therapy, and stem cell transplant. Any dosing schedules for such conventional cancer and/or anti-inflammatory treatments can also be used as determined by the skilled practitioner.

In various embodiments, the theranostic peptide agent is conjugated to a therapeutic agent as disclosed above. In various embodiments, the therapeutic agent is a cancer therapeutic and/or anti-inflammatory drug.

In various embodiments of the invention, the cancer therapeutic is a chemotherapy drug. Examples of cancer therapeutics include, but are not limited to, Platinum agents (cisplatin, carboplatin), Bevacizumab, Docetaxel, Camptothecin, Chlorin E6, Oxaliplatin, Carmustine, Cyclophosphamide, Vincristine, ixabepilone, Eribulin, Vinorelbine, Vinblastine, Irinotecan, Topotecan, Etoposide, Paclitaxel, Doxorubicin, Lomustine, Everolimus, Temozolomide, Taxotere, Pemetrexed, Cabazitaxel, Estramustine, Capecitabine, Gemcitabine, and Mitoxantrone. In various embodiments, the cancer therapeutic is cisplatin, docetaxel, camptothecin and/or chlorin E6.

In various other embodiments, the therapeutic agent is an anti-inflammatory drug. In some embodiments, the anti-inflammatory drug is a non-steroidal anti-inflammatory drug. In various other embodiments, the anti-inflammatory drug is an immune selective anti-inflammatory derivative. Examples of anti-inflammatory drugs include, but are not limited to, Aspirin, Ibuprofen, Paracetamol, Acetaminophen, Diclofenac, Naproxen, Meloxicam, Indomethacin, Metamizole, Celecoxib, Ketorolac, Ketoprofen, Piroxicam, Nimesulide, Etoricoxib, Mefenamic acid, Carprofen, Etodolac, Nabumetone, Flurbiprofen, Loxoprofen, Phenylbutazone, Sulindac, Aceclofenac, Dexketoprofen, Diflunisal, Benzydamine, Valdecoxib, Lornoxicam, Tenoxicam, Oxaprozin, Flunixin, Deracoxib, Fenoprofen, Tolmetin, Ethenzamide, Phenazone, Dexibuprofen, Lumiracoxib, Nepafenac, Bromfenac, and Fenbufen.

In various embodiments, the therapeutic agent is released all at once. In various embodiments, the therapeutic agent is adapted to be released in varying amounts at varying times. In various embodiments, the therapeutic agent can be released in small doses in a period of minutes, hours or days following administration of the theranostic peptide agent.

In various embodiments, the cancer is an Annexin 1 (ANXA1)-expressing cancer.

In various embodiments, the cancer is a formyl peptide receptor 1 (FPR1) expressing cancer.

Linkers

In various embodiments, a linker is used to conjugate the peptide ligand with the therapeutic agent and/or the imaging moiety. As used here in, linker and spacer are used interchangeably to refer to the stretch of molecules that are used to link together two molecules of interest. In various embodiments, the linker can be rigid, flexible or cleavable. Linkers are often composed of flexible residues like glycine and serine so that the adjacent protein domains are free to move relative to one another. In various other embodiments, the linker can comprise of different lengths. Linkers can be simple, for example, 1-10 amino acid linkers, comprising, e.g., lysine residues. Longer linkers are used when it is necessary to ensure that two adjacent domains do not sterically interfere with one another. Examples of linkers/spacers include, but are not limited to, lysine linkers, Beta-alanine, 4-aminobutyric acid (GABA), (2-aminoethoxy) acetic acid (AEA), 5-aminovaleric acid (AVA), 6-aminocaproic acid (Ahx), Fmoc-mini-PEGTM, 8-Amino-3,6-dioxaoctanoic acid (AEEA-[2-(2-Amino-ethoxy)-ethoxy]-acetic acid, mini-PEG1), Fmoc-8-Amino-3,6-Dioxaoctanoic Acid, 9-Fluorenylmethoxycarbonyl-8-Amino-3,6-Dioxaoctanoic Acid, Fmoc-AEEA, Fmoc-mini-PEG-3TM, 11-Amino-3,6,9-Trioxaundecanoic Acid, Fmoc-11-Amino-3,6,9-Trioxaundecanoic Acid, 9-Fluorenylmethoxycarbonyl-11-Amino-3,6,9-Trioxaundecanoic Acid, Fmoc-AEEEA ((2-[2-(2-Amino-ethoxy)-ethoxy]-ethoxy)-acetic acid), Boc-mini-PEGTM, Boc-8-Amino-3,6-Dioxaoctanoic Acid•DCHA, tert-Butyloxycarbonyl-8-Amino-3,6-Dioxaoctanoic Acid•Dicyclohexylamine, Boc-AEEA, Boc-mini-PEG-3TM, Boc-11-Amino-3,6,9-Trioxaundecanoic Acid•DCHA, tert-Butyloxycarbonyl-ll-Amino-3,6,9-Trioxaundecanoic Acid•Dicyclohexylamine, Boc-AEEEA, 12-amino-4,7,10-trioxadodecanoic acid (mini-PEG2), 15-amino-4,7,10,13-tetraoxapenta-decanoic acid (mini-PEG3), and Trioxatridecan-succinamic acid (Ttds). In various embodiments, the linker is a lysine linker or a PEG linker. In some embodiments, the linker is a lysine linker. In various other embodiments, the lysine linker comprises of more than one lysine (e.g., 2, 3, 4, 5, 6, 7, 8, 9, 10, 15, 20, 25, 30, 40, 50). In other embodiments, the linker is a PEG linker. In various other embodiments, the PEG linker can comprise of more than one PEG linker (e.g., 2, 3, 4, 5, 6, 7, 8, 9, 10, 15, 20, 25, 30, 40, 50). In yet other embodiments, the PEG linker can comprise 2 to 100 PEG linkers (e.g., 2-10, 10-20, 20-30, 30-40, 40-50, 50-75, 75-100).

Administration and Dosages

Various embodiments of the present invention provide for the administration of a multimodal peptide ligand imaging agent or a theranostic peptide agent that comprises a therapeutic drug to a subject with cancer and/or inflammation.

Examples of cancer include, but are not limited to, breast, brain, lung, pancreatic, kidney, stomach, uterine, cervical, colorectal, bladder, skin and/or head and neck cancer. In various embodiments, the cancer treated is breast cancer. In various other embodiments, the cancer treated is triple-negative breast cancer.

In various embodiments, the multimodal peptide ligand imaging agent and/or the theranostic peptide agent according to the invention may be formulated for delivery via any route of administration. "Route of administration" may refer to any administration pathway known in the art, including but not limited to aerosol, nasal, oral, transmucosal, transdermal or parenteral.

"Transdermal" administration may be accomplished using a topical cream or ointment or by means of a transdermal patch. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the ocular route, they may be in the form of eye drops.

In various embodiments, an agent can be administered intravenously by injection or by gradual infusion over time. Given an appropriate formulation for a given route, for example, agents useful in the methods and compositions described herein can be administered intravenously, intranasally, by inhalation, intraperitoneally, intramuscularly, subcutaneously, intracavity, and can be delivered by peristaltic means, if desired, or by other means known by those skilled in the art. In particular embodiments, compounds used herein are administered orally, intravenously or intramuscularly to a patient having cancer and/or inflammation. In various embodiments, the subject has breast cancer.

In various embodiments, the present invention provides the multimodal peptide ligand imaging agent and/or the theranostic peptide agent including a pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

In various embodiments, the present invention provides for the multimodal peptide ligand imaging agent and/or the theranostic peptide agent including a pharmaceutically acceptable excipient. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. The active ingredient can be mixed with excipients which are pharmaceutically acceptable and compatible with the active ingredient and in amounts suitable for use in the therapeutic methods described herein. Such excipients may be solid, liquid, semisolid, or, in the case of an aerosol composition, gaseous. Suitable excipients are, for example, starch, glucose, lactose, sucrose, gelatin, malt, rice, flour, chalk, silica gel, sodium stearate, glycerol monostearate, talc, sodium chloride, dried skim milk, water, saline, dextrose, propylene glycol, glycerol, ethanol, mannitol, polysorbate or the like and combinations thereof. In addition, if desired, the composition can contain minor amounts of auxiliary substances such as wetting or emulsifying agents, pH buffering agents and the like which enhance or maintain the effectiveness of the active ingredient. The therapeutic composition as described herein can include pharmaceutically acceptable salts. Pharmaceutically acceptable salts include the acid addition salts formed with inorganic acids such as, for example, hydrochloric or phosphoric acids, organic acids, for example, acetic, tartaric or mandelic, salts formed from inorganic bases such as, for example, sodium, potassium, ammonium, calcium or ferric hydroxides, and salts formed from organic bases such as isopropylamine, trimethylamine, 2-ethylamino ethanol, histidine, procaine and the like. Liquid compositions can contain liquid phases in addition to and in the exclusion of water, for example, glycerin, vegetable oils such as cottonseed oil, and water-oil emulsions. Physiologically tolerable carriers are well known in the art. The amount of an active agent used in the invention that will be effective in the treatment of a particular disorder or condition will depend on the nature of the disorder or condition, and can be determined by one of skill in the art with standard clinical techniques.

The multimodal peptide ligand imaging agent and/or the theranostic peptide agent, according to the invention, can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The theranostic peptide agent, according to the invention, may be delivered in a therapeutically effective amount. The precise therapeutically effective amount is that amount of the therapeutic agent that will yield the most effective results in terms of efficacy of treatment in a given subject. This amount will vary depending upon a variety of factors, including but not limited to the characteristics of the therapeutic agent (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts can determine a therapeutically effective amount, for instance, by monitoring a subject's response to administration of a compound and adjusting the dosage accordingly. For additional guidance, see *Remington: The Science and Practice of Pharmacy* (Gennaro ed. 20th edition, Williams & Wilkins PA, USA) (2000).

Typical dosages of an effective theranostic peptide agent can be as indicated to the skilled artisan by the in vitro responses or responses in animal models. Such dosages typically can be reduced by up to about one order of magnitude in concentration or amount without losing the relevant biological activity. Thus, the actual dosage can depend upon the judgment of the physician, the condition of the patient, and the effectiveness of the therapeutic method based, for example, on the in vitro responsiveness of the relevant primary cultured cells or histocultured tissue sample, such as biological samples obtained, or the responses observed in the appropriate animal models.

For the treatment of cancer and/or inflammation, the appropriate dosage of the pharmaceutical composition comprising the theranostic peptide agents of the present invention depends on the type of disease to be treated, the severity and course of the disease, the responsiveness of the disease, whether the agent is administered for therapeutic or preventative purposes, previous therapy, and patient's clinical history. The dosage can also be adjusted by the individual physician in the event of any complication and at the discretion of the treating physician. The administering physician can determine optimum dosages, dosing methodologies and repetition rates. The theranostic peptide agent can be administered one time or over a series of treatments lasting from several days to several months, or until a cure is effected or a diminution of the disease state is achieved (e.g., treatment or amelioration of cancer and/or inflammation). In various embodiments, the multimodal peptide ligand imaging agent can be used to monitor the progress of administered treatment and or disease amelioration. The duration of treatment depends upon the subject's clinical progress and responsiveness to therapy. In certain embodiments, the dosage of the therapeutic agent is from 0.01 µg to 100 mg per kg of body weight, and can be given once or more daily, weekly, monthly or yearly. For systemic administration, subjects can be administered a therapeutic amount, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

Imaging

Various embodiments of the present invention provide for the administration of the multimodal peptide ligand imaging agent comprising an imaging moiety, to target and visualize cancer and/or inflammatory cells to be treated or to monitor treatment progress. In various embodiments, multimodal peptide ligand imaging agent is administered in an amount sufficient to image and detect the imaging moiety using imaging techniques readily available and known to one of skill in the art. In various embodiments, the multimodal peptide ligand imaging agent is administered only once for imaging. In other embodiments, the multimodal peptide ligand imaging agent is administered in a series of administrations for multiple imaging options. In various other embodiments, the multimodal peptide ligand imaging agent is administered in a dose of about 0.5-10 nM. In other embodiments, the dosage can be from about 0.5-5 nM or 5-10 nM. In yet other embodiments, the dosage can be from about 0.5 to 1 nM, 1-2 nM, 2-3 nM, 3-4 nM, 4-5 nM, 5-6 nM, 6-7 nM, 7-8 nM, 8-9 nM or 9-10 nM.

In various embodiments, the imaging moiety of the multimodal peptide ligand imaging agent is imaged once or in a series of images following administration of the multimodal peptide ligand imaging agent. In various other embodiments, the multimodal peptide ligand imaging agent is administered prior to, simultaneously as or subsequent to treatment.

In various embodiments, the imaging moiety can be imaged using the methods of optical/fluorescence imaging, SPECT imaging, PET imaging and/or MRI. Examples of the imaging moiety include, but are not limited to, optical fluorescence imaging (FITC, cy5, cy7, IRdye-800); SPECT imaging ($^{99m}$Tc, $^{111}$In, $^{123}$I, $^{125}$I); PET imaging ($^{18}$F, $^{11}$C, $^{68}$Ga, $^{64}$Cu, $^{89}$Zr, $^{124}$I); and MRI (gadolinium, $^{19}$F, $^{31}$P, Superparamagnetic iron oxide).

Kits

The present invention is also directed to a kit to treat cancer and/or inflammation. The kit comprises of the peptide agents described herein, which can be used to perform the methods described herein. The kit is useful for practicing the inventive method of providing treatment to a subject with cancer and/or inflammation by administering a theranostic peptide agent. The kit is an assemblage of materials or components, including at least one of the inventive compositions. Thus, in some embodiments the kit contains a composition including the theranostic peptide agents of the present invention, for the treatment of cancer and/or inflammation, as described above. In various other embodiments, the kit contains a composition including a multimodal peptide ligand imaging agent for the diagnosis, prognosis and/or staging of cancer and/or inflammation.

The exact nature of the components configured in the inventive kit depends on its intended purpose. For example, some embodiments are configured for the purpose of treating cancer and/or inflammation. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treat or alleviate cancer and/or inflammation. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example, the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging materials employed in the kit are those customarily utilized in the administration of treatments. As used herein, the term "package" refers to a suitable solid matrix or material such as glass, plastic, paper, foil, and the like, capable of holding the individual kit components. Thus, for example, a package can be a glass vial or prefilled syringes used to contain suitable quantities of an inventive composition containing the peptide agents described herein. The packaging material generally has an external label which indicates the contents and/or purpose of the kit and/or its components.

EXAMPLES

The following examples are not intended to limit the scope of the claims to the invention, but are rather intended to be exemplary of certain embodiments. Any variations in the exemplified methods which occur to the skilled artisan are intended to fall within the scope of the present invention.

Example 1

The multimodal peptide imaging agent comprises of the base sequence of the peptide ligand: Leu-Asp-Leu-Leu-Asp-Leu (LDLLDL; SEQ ID NO:1) and an imaging moiety (M)-(LDLLDL-K-M, [SEQ ID NO:1]-K-M; FIG. 1). The imaging moieties were conjugated with the peptide through a lysine (K) spacer (also referred herein as a linker). M represents imaging probes for multimodality imaging, including nuclear imaging radioisotopes, MRI imaging probes, and near infrared fluorophores (NIRF).

TABLE 1

| Examples of Imaging Moieties | |
|---|---|
| Optical imaging | FITC, cy5, cy7, IRdye-800 |
| SPECT imaging | $^{99m}$Tc, $^{111}$In, $^{123}$I, $^{125}$I |
| PET imaging | $^{18}$F, $^{11}$C, $^{68}$Ga, $^{64}$Cu, $^{89}$Zr, $^{124}$I |
| MRI | gadolinium, $^{19}$F, $^{31}$P, Superparamagnetic iron oxide |

Figure 2:
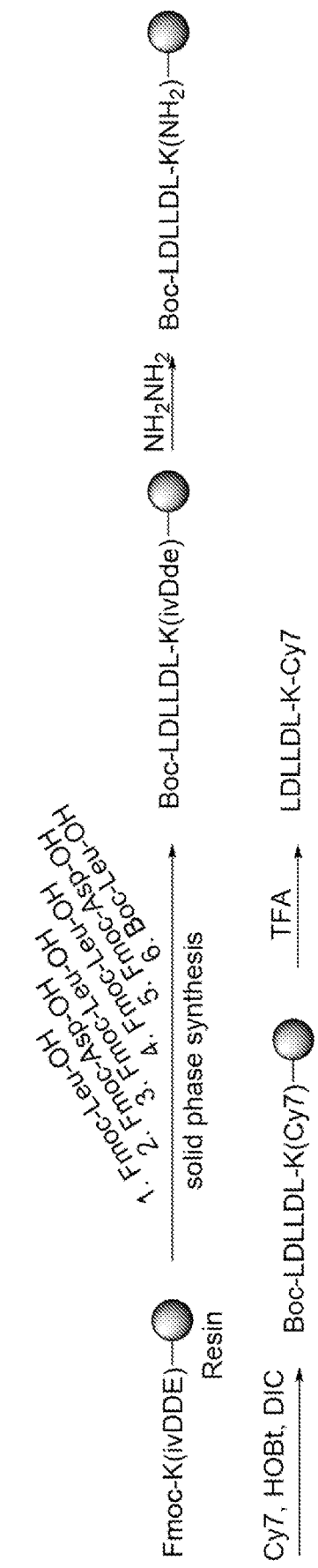
FIG. 2 depicts in accordance with various embodiments of the invention, a schematic of the synthesis of LDLLDL-K-Cy7 ([SEQ ID NO:1]-K-Cy7) for NIRF imaging.

The synthesis of peptide imaging agents is demonstrated by the synthetic scheme of NIRF imaging probe (FIG. 2). The base peptide ligand was synthesized by the solid-phase method. The peptide sequence was assembled on resin and cleaved from the solid support with TFA. The imaging moiety was conjugated with the ω-amino group of the lysine.

Figure 3:
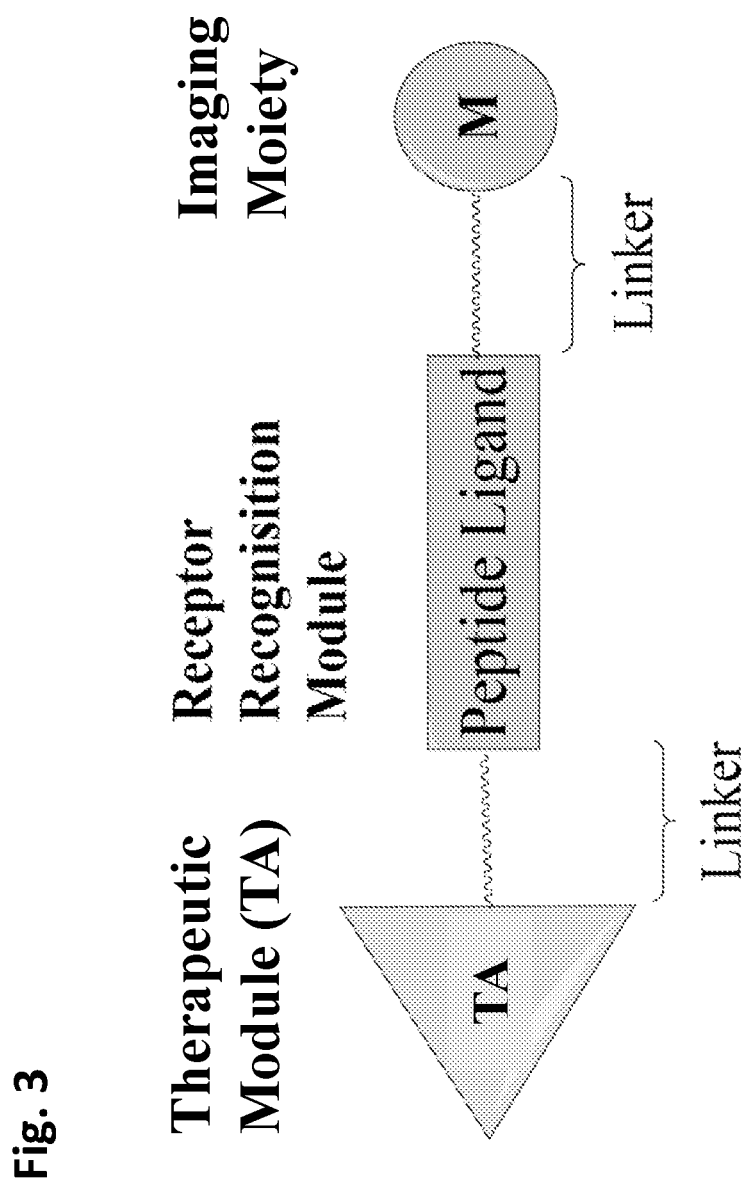
FIG. 3 depicts in accordance with various embodiments of the invention, a theranostic peptide agent. A therapeutic drug, covalently conjugated with the peptide ligand through amide bonds. The resulting theranostic peptide agent with therapeutic drug and imaging probe can deliver drugs to cancer cells via the FPR1 receptor, while being able to visualize targeted tissue via imaging methods.

The theranostic peptide agent comprises the multimodal peptide imaging agent (imaging moiety) and a therapeutic module comprising a therapeutic agent (TA)-(TA-LD-LLDL-M (TA-[SEQ ID NO:1]-M); FIG. 3).

The inventors performed studies with the peptide agent using in vitro in vivo experiments.

In Vitro Studies

Figure 4:
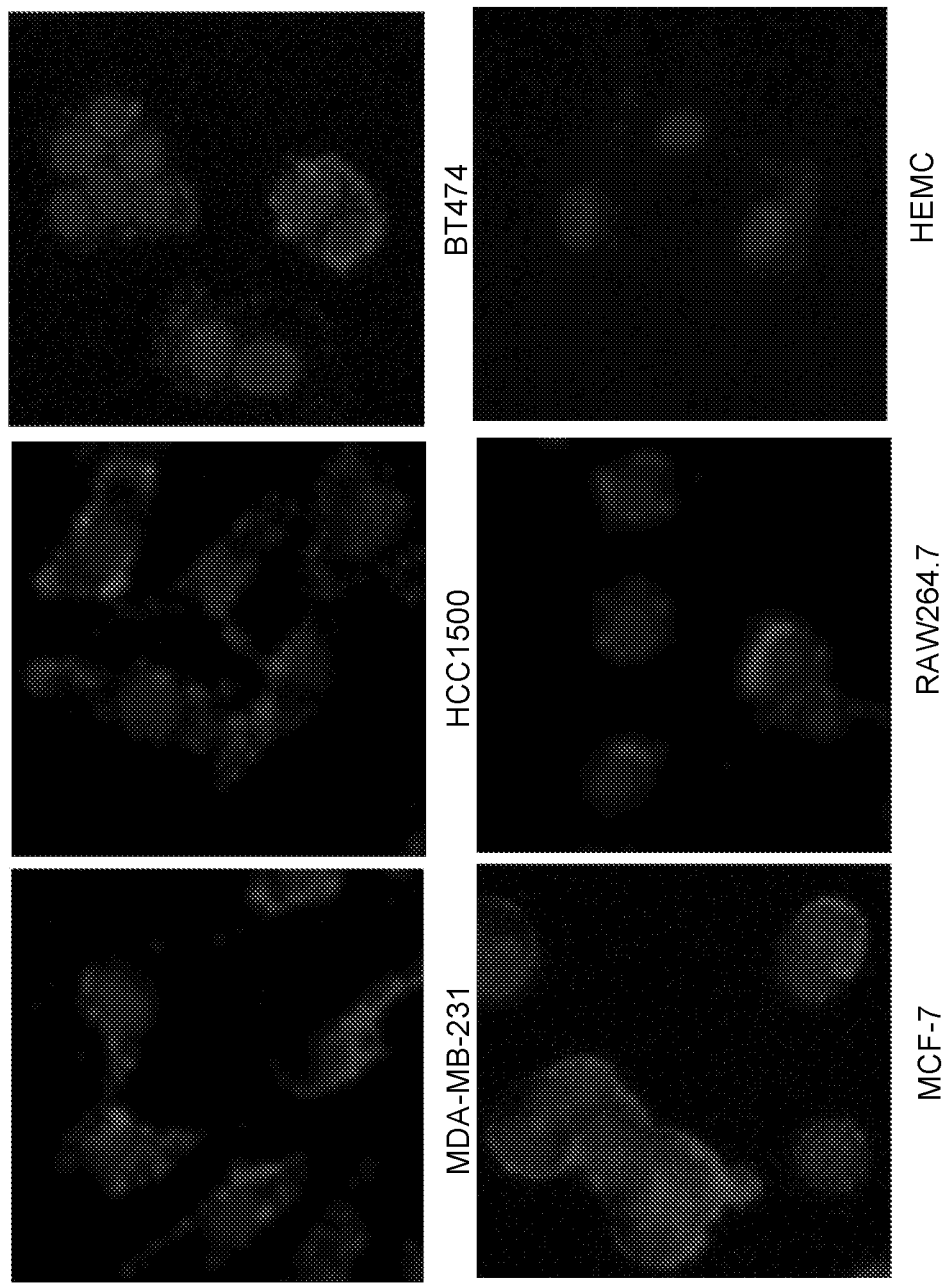
FIG. 4 depicts in accordance with various embodiments of the invention, fluorescence imaging of breast cancer cell lines (MDA-MB-231, HCC1500, BT474, MCF-7) and macrophage cell line (RAW264.7) as well as normal human mammary epithelial cell (HEMC) incubated with FPR peptide for 4 hours.

To study the ability of the FPR peptide to internalize and fluorescently labeled cancer and macrophage cells, various breast cancer cell lines were treated with the peptide (5 uMol/uL) for 4 hrs. All cells were imaged using near infrared fluorescence imaging, as shown in FIG. 4. Results show cell associated fluorescence in all cancer cells, including two triple-negative breast cancer (MDA-MB-231, and HCC1500), Her2 (BT474), and luminal A (MCF-7) cell lines. The macrophage activated cell (RAW264.7) also demonstrate substantial uptake of the peptide. Fluorescence uptake was not observed in the normal human mammary epithelial cells (HEMC-control), as expected, since there is no expression of FPR receptor for HEMC.

In Vivo Studies

Figure 6:
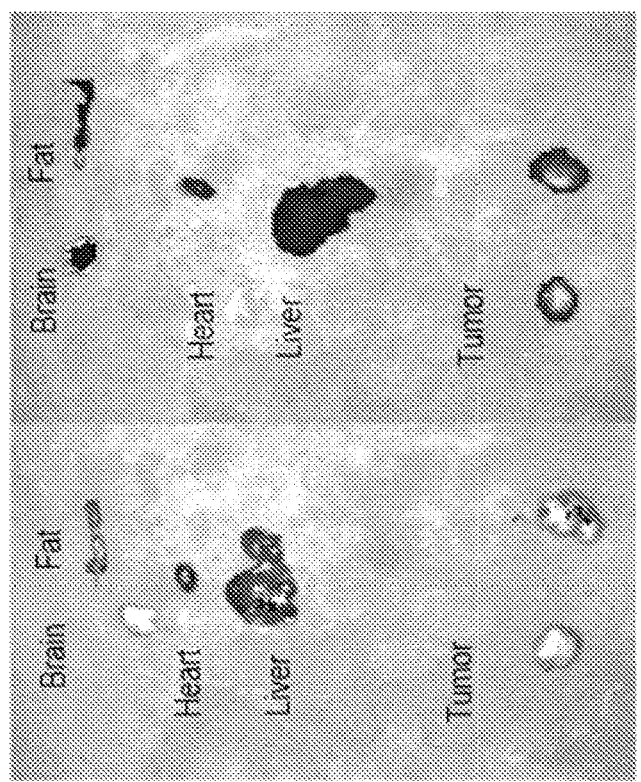
FIG. 6 depicts in accordance with various embodiments of the invention, the biodistribution in tumor-bearing mice after 7 hours of tail vein injection. Mice were injected with fluorescent dye only (left panel), and peptide LDLLDL-Cy7 (right panel)([SEQ ID NO:1]-Cy7).
Figure 5:
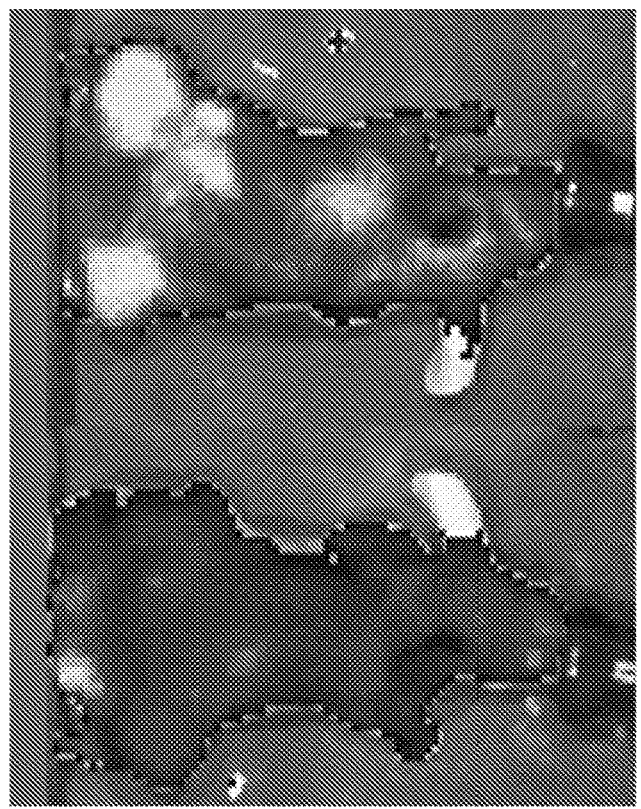
FIG. 5 depicts in accordance with various embodiments of the invention, in vivo fluorescent image of xenograft mice after 6 hours of tail vein injection. Mice were injected with fluorescent dye (Cy7) only (left panel), and peptide-Cy7 (right panel).

Ten mice were implanted with breast cancer cells (MDA-MB-231) to develop breast cancer tumor xenograph models. The tumors were allowed to grow for 4 weeks before the mice were injected with 30 ul of peptide (2 nMoles). The animals were imaged using mouse fluorescence imaging after 1, 2, 3, 4, and 6 hours. FIG. 5 show the results of one of those mice experiments. Within 6 hours, intense fluorescence is already observed within the implanted breast cancer tumors (FIG. 5—right panel). On the contrary, the control mice injected with the dye (Cy7) alone has no residual fluorescence in the tumor after 6 hours (FIG. 5—left panel). After 7 hours the animals were sacrificed and organs extracted and imaged. Results demonstrate strong uptake of the peptide in the tumors, and no significant fluorescence in the rest of the organs (FIG. 6).

Example 2

Breast cancer can be classified into five molecular subtypes, including luminal A and B, HER2, triple-negative (basal-like), and normal-like phenotypes. Triple-negative breast cancer (TNBC) is a subset of cancers which do not express the three most common molecular markers, namely the estrogen receptor (ER), progesterone receptor (PR), and HER2/neu. These cancers are well known for aggressive behavior and poor prognosis. The majority of TNBCs are aggressive basal-like subtypes presenting with larger tumors of higher grade, and increased numbers of involved nodes.

Multimodality imaging has been used in breast cancer diagnosis, including ultrasound, X-ray mammogram, MRI, CT and PET. Even though much effort has been spent to identify breast phenotype differences using currently available diagnostic imaging, the results still are not well correlated to the intrinsic tumor biology function, and are difficult to adapt into clinic relevance due to the complex nature of the disease. Currently, the only reliable TNBC diagnosis method is immunohistochemistry (IHC) via tissue biopsy for evaluation of expression of ER, PR and HER2. However, such IHC techniques remain inconvenient and may be biased by biopsy location or specimen selection from resected tumor tissue.

PET imaging in TNBC patients using $^{18}$F-FDG PET/CT has been used in diagnosis and tumor staging in breast cancer. Recent studies show FDG-PET has prognostic value to classify different breast cancer phenotypes. A recent study by the inventors further showed that PET imaging can stratify the prognosis of TNBC patients. Pre-treatment PET/CT images of two TNBC cases demonstrate the association between PET uptake and patient survival: good prognosis with low maximum standard uptake value (SUVmax) and poor prognosis with high SUVmax. Although these studies suggest the potential clinical benefit, clinical implementation of PET is still under debate. The main criticism of the use of PET is that the connection between imaging features and intrinsic cancer biological function is still unknown. It is thus essential to develop a tumor-gene-specific PET imaging probe which integrates clearly identified tumor biology and visible imaging features.

Annexin A1 (ANXA1) is a calcium-dependent phospholipid-linked protein which is involved in anti-inflammatory effects, regulation of cellular differentiation, proliferation and apoptosis. Multiple clinical studies, including the inventors', show that ANXA1 is overexpressed in TNBC, and is significantly associated with poor patient outcome of breast cancer patients. The functional analysis of ANXA1 in breast cancer cell lines shows it is involved in tumorigenesis and migration, and the suppression of ANXA1 expression through siRNA knockdown results in significant reduction of the cellular invasion ability and metastatic potential. Several studies further show that ANXA1 may increase metastatic potential through the regulation of NF-κB in breast cancer, and may promote metastasis formation by enhancing the TGFβ/Smad signaling pathway.

Studies have shown that ANXA1 must be externalized by its cellular sources before exerting its cellular effects. However, ANXA1 itself lacks a signal peptide, and externalization of ANXA1 must be activated via interaction with FPRs. The FPRs are a family of seven transmembrane domains, G protein-coupled receptors that are expressed mainly in mammalian phagocytic leukocytes. To date, FPRs are the only known receptors of externalized ANXA1. Studies have shown that ANXA1 triggered the FPRs and stimulated cell invasion by extracellular signal-related kinase phosphorylation and subsequent integrin β1-binding protein expression. Without being bound to any particular theory, mounting evidence suggests that FPRs can be used as surrogates for evaluation of ANXA1 activation. Thus, FPR1 was selected as a target surrogate for ANXA1 in breast cancer.

The synthesized FPR peptide PET imaging probe provides a method for monitoring ANXA1 expression in aggressive breast cancer which can then proceed to further development as a clinical imaging biomarker. The imaging approach can be used as an effective staging tool for monitoring disease development, and should improve the accuracy of diagnosis of aggressive breast cancer, as well as laying a foundation for using the FPR peptide as an imaging biomarker to predict response to cancer treatment.

Diagnostic Approach for Aggressive Breast Cancer

Results indicate that the ANXA1 gene is significantly associated with aggressive breast cancer, and can be effectively monitored via FPR expression. Without being bound to any particular theory, the inventors believe that the FPR binding receptor can be developed into a molecular imaging agent for detection of ANXA1-expressing breast carcinomas. In the inventors' studies, the inventors identified a novel peptide, Leu-Asp-Leu-Leu-Asp-Leu (LDLLDL; SEQ ID NO:1), which specifically binds to FPR1 receptor and can be labeled by fluorescence or radioisotopes. LDLLDL (SEQ ID NO:1) is a hexapeptide antagonist that binds to but does not activate the receptor. This peptide also exhibits superior solubility and target affinity, making LDLLDL (SEQ ID NO:1) suitable for use in the present invention to monitor the ANXA1/FPR1 expression in the process of tumorigenesis and progression.

The $^{64}$Cu radionuclide (half-life, 12.7 h; decay characteristics β+ 19%, β-40%) is produced in a cyclotron with high specific activity and is easily supplied as $^{64}$CuCl$_2$ in HCl solution. LDLLDL (SEQ ID NO:1) radiolabeled with $^{64}$Cu will provide favorable tumor sensitivity and tissue penetration. The physical characteristics of $^{64}$Cu will allow radiolabeled LDLLDL (SEQ ID NO:1) to be easily implemented in clinical use.

Described herein are the development and study of an imaging probe for aggressive breast cancer with a number of highly significant capabilities. The PET imaging probe, LDLLDL-$^{64}$Cu ([SEQ ID NO:1]-$^{64}$Cu), is a molecular-genetic imaging agent which provides spatio-temporal visualization of tumor cellular processes at a molecular or genetic level. Relying on tracking intrinsic microenvironment cancer biology, this probe allows the visualization of tumorigenesis, formation, progression and migration of breast cancers. This tumor-specific molecular imaging is extremely valuable for the early diagnosis and staging of TNBC patients, including the early identification of aggressive subtypes, allowing patients to be quickly and non-invasively screened while helping identify patients who may benefit from targeted therapies for TNBC. The potential for monitoring progression of TNBC will also make this new technique highly valuable for applications requiring treatment response evaluation which can lead to important improvements in our ability to effectively treat triple negative breast cancer.

The inventors describe herein a new generation of tumor specific imaging agents for aggressive breast cancer with the following innovative features: 1) Use of a FPR1 peptide that targets ANXA1-expressing breast cancer as a diagnostic strategy for TNBC. Currently, there is no effective non-invasive approach that can quickly detect aggressive breast cancer: non-target-specific PET imaging suffers high false negative rates. The peptide-based probe developed by the inventors allows accurate identification of the tumor genetic active region and ensure early disease detection. 2) Use of molecular-genetic imaging which integrates detection of microenvironment and global visible tumor characteristics. Compared with currently available diagnostic imaging, the method described herein provides not only global tumor geometry and morphology but also cellular-level functions, such as tumor formation, progression, and migration, so the imaging can be correlated with intrinsic cancer biology functions. 3) Use of the peptide LDLLDL (SEQ ID NO:1) to specifically target cancer has not been reported in either the cancer research or molecular imaging fields. The chemical synthesis of this peptide probe is simple and straightforward, making this compound suitable for targeting various cancer and/or tumors, including breast cancer. Due to the non-toxic, biocompatible and biodegradable properties of the peptide molecules, this agent can be used as a carrier molecule for delivery of therapeutic payload into tumors for cancer targeted therapy as described herein. FPRs are the only known receptors of externalized ANXA1, and can be activated by the N-terminal peptide cleaved from ANXA1. The ANXA1/FPR complex participates in tumorigenesis and cancer progression in different ways.

Additional Studies

A FPR-targeted peptide and its optical imaging probe were designed and synthesized: The inventors synthesized an FPR-targeted peptide agent Leu-Asp-Leu-Leu-Asp-Leu (LDLLDL: SEQ ID NO:1), which is an antagonist peptide for FPR1 receptor. The inventors have also developed an NIR optical imaging probe to evaluate the targeting capability. Specifically, the base peptide ligand was synthesized by the solid-phase method. After the peptide sequence was assembled on resin, the ivDDE protecting group was removed from the w-amino group of the lysine by treatment with hydrazine. The inventors tested varying concentrations (0.1-1000 μM/mL) of LDLLDL (SEQ ID NO:1) peptide in all four breast cancer cell types (BT474, BT549, MDA-MB-231 and MCF-7) to assess cellular toxicity. Apparent cell death could not be observed by microscopy even for the highest concentration tested.

LDLLDL-Cy7 ([SEQ ID NO:1]-Cy7) was used to treat five cancer cell lineages (MDA-MB-231, BT549, HCC1500, BT474, and MCF-7) and normal human mammary epithelial cell (HEMC) for 3 hrs at the concentrations of 5 and 10 μM/mL. After washing 3 times with cold PBS, all cells were imaged using near infrared fluorescence imaging and target specificity of the FPR peptide was evaluated. High binding affinity was observed in human TNBC cells.

Results demonstrate that substantial uptake (FIG. 4) of LDLLDL-Cy7 ([SEQ ID NO:1]-Cy7) was observed in the two triple-negative breast cancer lines (MDA-MB-231, HCC1500) while weak uptake was observed in HER2 (BT474) and luminal A (MCF-7) cell lines. Nonetheless, uptake was observed in HER2 (BT474) and luminal A (MCF-7) cell lines. As expected, no fluorescence uptake was observed in the normal human mammary epithelial cell (HEMC).

Several inflammation and neutrophil-specific PET and SPECT imaging probes have been developed. In early studies, the inventors developed a peptide imaging probe cFLFLF-PEG76-$^{64}$Cu for evaluating lung inflammation using PET imaging. The results showed that the probe exhibits strong neutrophil binding in a mouse model of pneumonia infection. A neutrophil-targeting SPECT imaging probe, cFLFLFPEG-TKPPR-99mTc, has also been developed and has demonstrated its inflammation targeting specificity using a mouse model of ear inflammation.

Synthesis and In Vitro Evaluation of $^{64}$Cu Labeled FPR Peptide PET Imaging Probe ($^{64}$Cu-LDLLDL ($^{64}$Cu-[SEQ ID NO:1]).

The inventors have successfully synthesized a FPR1 peptide, LDLLDL (SEQ ID NO:1), and its optical imaging probe for tumor targeting. Without being bound to any particular theory, the inventors believe that the $^{64}$Cu labeled LDLLDL (SEQ ID NO:1) will target tumor-expressing ANXA1 with excellent target binding specificity. The inventors demonstrate tumor-targeted specificity in cellular uptake and in vivo 3D fluorescence molecular imaging. $^{64}$Cu when conjugated with a synthetic LDLLDL (SEQ ID NO:1) peptide having affinity for tumor expressing ANXA1, targets and accumulates with high uptake at the tumor site, as shown by in vivo fluorescence (FIGS. 5 and 6). LDLLDL-$^{64}$Cu ([SEQ ID NO:1]-$^{64}$Cu) targets tumor-expressing ANXA1 with excellent specificity and sensitivity in human breast cancer cell models.

The inventors synthesized LDLLDL-$^{64}$Cu ([SEQ ID NO:1]-$^{64}$Cu) and tested its properties in vitro, including partition coefficient, serum stability, cytotoxicity, plasma half-time and decay functions. Nonradioactive peptide LDLLDL-Copper ([SEQ ID NO:1]-Copper) was also synthesized for competition binding and biological assay. The ANXA1 binding specificity was examined by measuring radiation disintegrations with multiple breast cancer cell lines. Baseline ANXA1 expression is evaluated by western blotting and qRT-PCR using anti-ANXA1 and anti-FPR1 antibodies.

Methods

Figure 7:
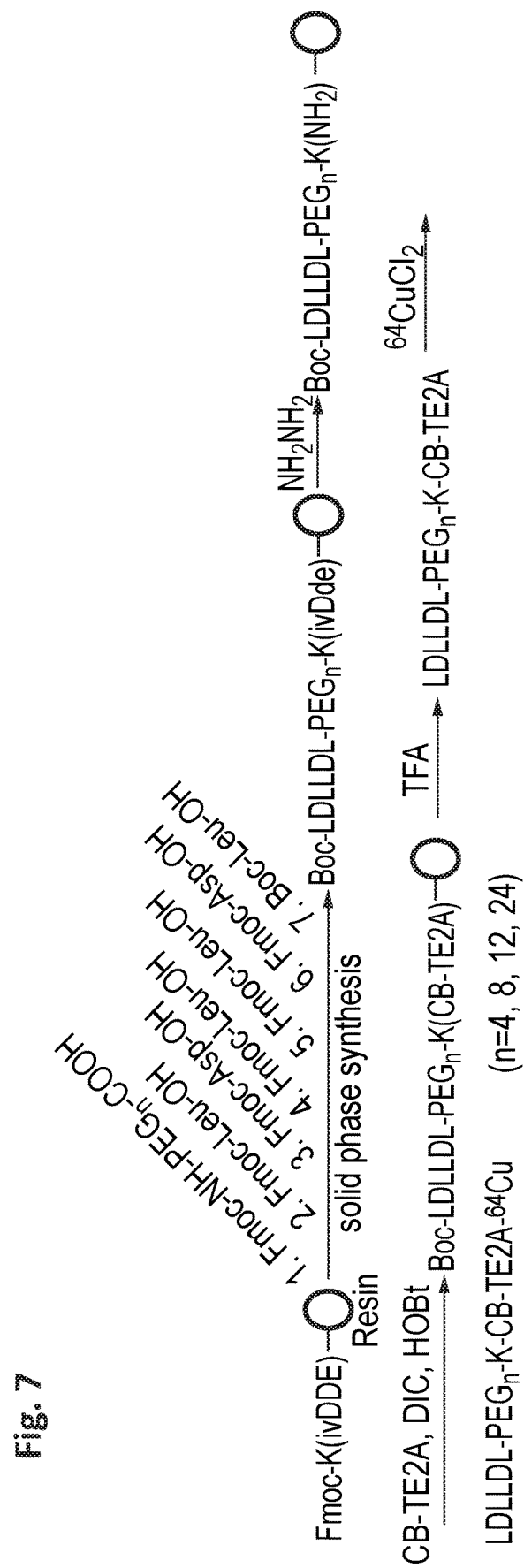
FIG. 7 depicts in accordance with various embodiments of the invention, a schematic of the synthesis of LDLLDL-$^{64}$Cu ([SEQ ID NO:1]-$^{64}$Cu) for PET imaging.

The synthesis of LDLLDL-$^{64}$Cu ([SEQ ID NO:1]-$^{64}$Cu) peptide is performed in three stages: i) The base peptide LDLLDL (SEQ ID NO:1) is synthesized as described above. ii) The molecular structure is further modified to gain desired pharmacological characteristics. Specifically, a bifunctional polyethylene glycol (PEG)n (n=4, 8, 12, 24) moiety is conjugated to the peptide C-terminal, and an additional lysine residue will be incorporated in the construct at the PEG end as a handle for the chelating group and its coordination to the radiometal. The amino group will be used for conjugation with chelators for radiolabeling. iii) CB-TA2A (1,4,8,11-Tetraazabicyclo[6.6.2] hexadecane-4,11-diacetic acid) is used as the chelator for $^{64}$Cu radiolabeling. CB-TE2A, commercially available from Macrocyclics (Dallas, Tex.), is a highly water soluble, non-toxic ligand having very strong affinity for copper. iv) The peptide is finally conjugated with the positron emitting radionuclide $^{64}$Cu. The scheme of synthesis of LDLLDL-PEGnK(CB-TE2A)-$^{64}$Cu ([SEQ ID NO:1]-PEGnK(CB-TE2A)-$^{64}$Cu), (still called LDLLDL-$^{64}$Cu [SEQ ID NO:1]-$^{64}$Cu for simplicity), is shown in FIG. 7. The PEGylated peptide and its CE-TE2A conjugates will be synthesized by the solid-phase method via Fmoc strategy, using 2-(1H-benzotriazole-1-yl)-1,1,3,3-tetramethyluronium hexafluorophosphate (HBTU) as the coupling agent on a CS136XT automated peptide synthesizer. After peptide sequences are assembled on 2-Chlorotrityl or Wang Resin, the products are cleaved from the solid support. The resulting crude products are purified by RPHPLC. $^{64}$CuCl2 is added to LDLLDL-PEGnK(CB-TE2A) ([SEQ ID NO:1]-PEGnK(CB-TE2A)) in 0.1 M NH4OAc (pH 5.5), and heated at 95° C. for 1 h. Using the same strategy, nonradioactive LDLLDL-Copper ([SEQ ID NO:1]-Copper) is synthesized.

Purification and characterization, chemical and radiochemical purity analysis is done using a semi-preparative reversed phase high-performance liquid chromatography (RP-HPLC) for product purification on an Agilent system and an Apollo C18 reversed-phase column (5 μm, 250×10 mm). Matrix-assisted laser desorption/ionization time-of-flight (MALDI-TOF) or electrospray ionization (ESI) mass spectrometry analysis is performed on all peptide products. The radiolabeled compound is compared with its cold (non-radiolabeled) counterpart for further confirmation of the structure. The LDLLDL-$^{64}$Cu ([SEQ ID NO:1]-$^{64}$Cu) PET imaging agent is analyzed for its pharmacological function on cancer cell lines.

Partition coefficient (Log P) values are determined by measuring its octanol-water partition value of LDLLDL-$^{64}$Cu ([SEQ ID NO:1]-$^{64}$Cu). Approximately 300 kBq of LDLLDL-$^{64}$Cu ([SEQ ID NO:1]-$^{64}$Cu) in 500 μL of water is mixed with the solution with 500 mL of octanol in an Eppendorf microcentrifuge tube. The tube is sonicated for 10 min and then centrifuged at 4,000 rpm for 5 min. Radioactivity is measured in 100 mL aliquots of both octanol and water layers in triplicate. Approximately 100 μCi of the LDLLDL-$^{64}$Cu ([SEQ ID NO:1]-$^{64}$Cu) is added to 500 μL of rat serum (Sigma Chemical Co.) Serum stability of LDLLDL-$^{64}$Cu ([SEQ ID NO:1]-$^{64}$Cu) is determined by incubation in 37° C. for a series of time points and the ratio of intact and degraded probe is measured by analytical radio-HPLC.

In vitro cytotoxicity assays will be performed on breast cancer cells (MDA-MB-231, BT549, MFC-7) and normal epithelial cells HEMC. For cytotoxicity studies a series of concentrations of nonradioactive LDLLDL-Copper ([SEQ ID NO:1]-Copper) solution will be tested and equal volumes of PBS are added as a control. After incubation, the media is replaced with a 270 μl fresh one, and then 30 d MTT ((3-(4, 5-dimethylthiazolyl-2)-2 5-diphenyltetrazolium bromide) solution is added into each well and followed by an additional 4 hour incubation. The media is finally removed and replaced with 200 μl DMSO to dissolve crystals, and absorption at 595 nm is measured with a plate reader. IC50 values are determined by nonlinear regression analysis.

In vitro target specificity binding is evaluated in two steps: Step 1: Characterize the ANXA1/FPR1 expression baseline by examining expression levels of FPR1 and ANXA1 in five human breast cancer cell lines, MDA-MB-231, HCC1500, BT549, MCF-7, BT474, and HEMC. Obtaining protein expression by performing IHC staining using the anti-ANXA1 and anti-FPR1 antibody. The cell lines with positive staining are identified. Further, the transcriptional level of ANXA1 and FPR1 are evaluated by western blotting and qRT-PCR. The correlation between FPR1 and ANXA1 are validated, and the cells with highest FPR1 and ANXA1 expression are selected for further in vivo study. The results establish the baseline of expression of ANXA1 and FPR1 in the tested breast cancer cell lines.

Step 2: Characterization of the binding specificity of the LDLLDL-$^{64}$Cu ([SEQ ID NO:1]-$^{64}$Cu) is tested on the cell lines described above. The cells are cultured in two groups of Petri dishes. For group 1, cells ($2\times10^5$ cells per tube) are incubated with LDLLDL-$^{64}$Cu ([SEQ ID NO:1]$^{64}$Cu) ($1\times10^5$ counts per min) for different times (3, 5, 10, 20, 30, 40, and 60 min) at 37° C. After incubation, the medium is removed and the cells are rinsed and centrifuged. The suspended cells are measured for radioactivity using a gamma-counter. Disintegrations per minute per cell are calculated and reported as the peptide uptake for each cell line. For group 2, a competitive binding assay with nonradioactive LDLLDL-Copper ([SEQ ID NO:1]-Copper) is performed to determine the 50% inhibitory concentration (IC50). Cells are pre-saturated with 1000-fold excess of nonradioactive LDLLDL-Copper ([SEQ ID NO:1]-Copper) peptide for about 30 min before adding the radioisotope-labeled peptide. The cell-associated radioactivity is measured, and the binding affinity is determined by the Grafit software (Erithacus, Inc). Finally, the results of radioisotope-peptide uptake are correlated to the base line measures from step 1.

Figure 8:
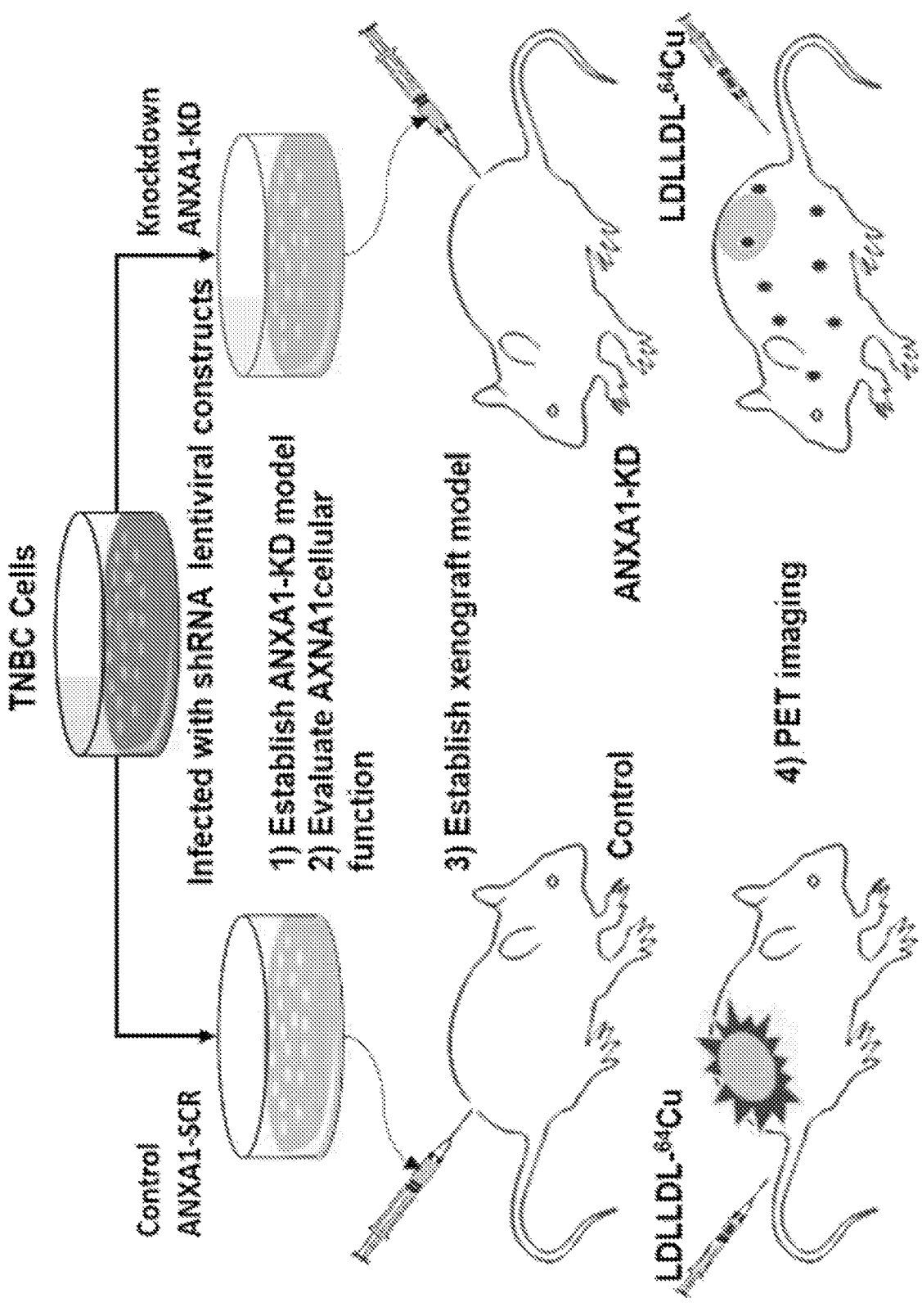
FIG. 8 depicts in accordance with various embodiments of the invention, experimental methods for characterizing target binding of LDLLDL-$^{64}$Cu in vivo ([SEQ ID NO:1]-$^{64}$Cu)).
Figure 10:
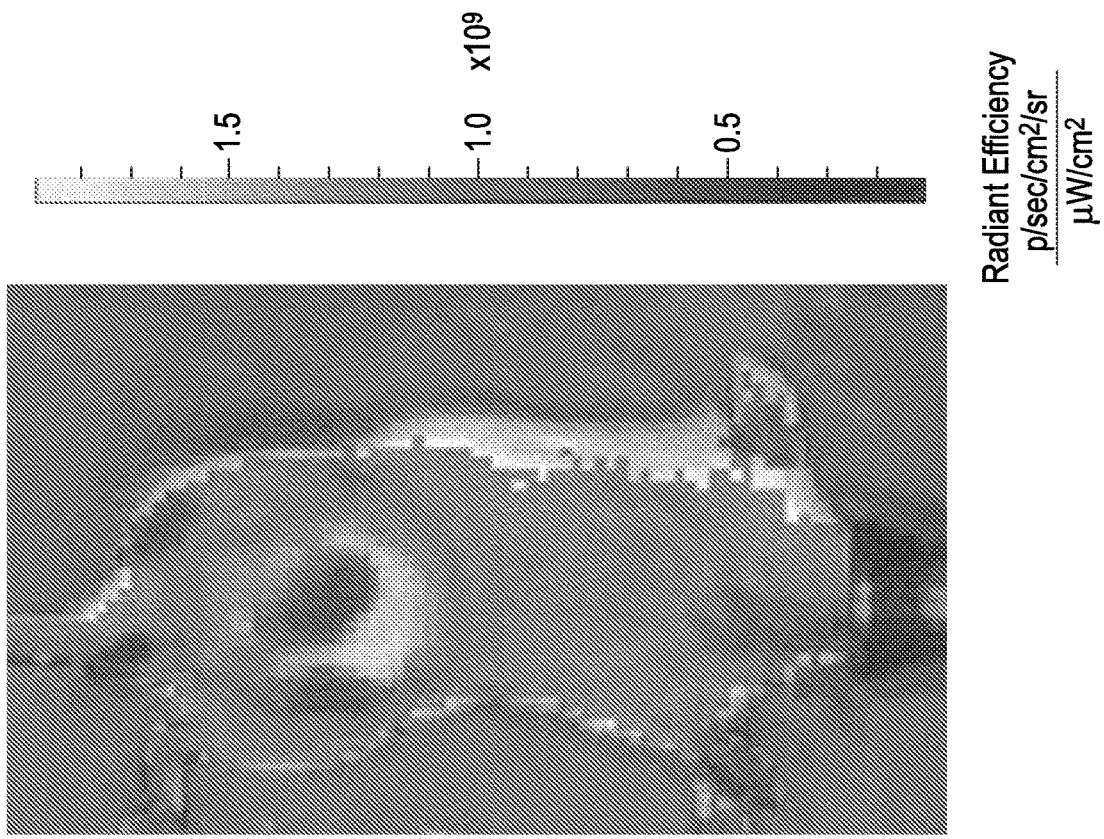
FIG. 10 depicts one of 10 mice experiments in accordance with various embodiments. Ten mice (Balb/c mice) were implanted with breast cancer cells (4T1) to develop breast cancer tumor xenograph model. The tumors were allowed to grow for 4 weeks before the mice were injected with 30 ul of peptide (2 nMoles). The animals were imaged using mouse fluorescence imaging after 1, 2, 3, 4, 6 hr. Notice that within 6 hr, intense fluorescence is already observed within the implanted breast cancer tumors on the mammary gland of the mice.
Figure 9:
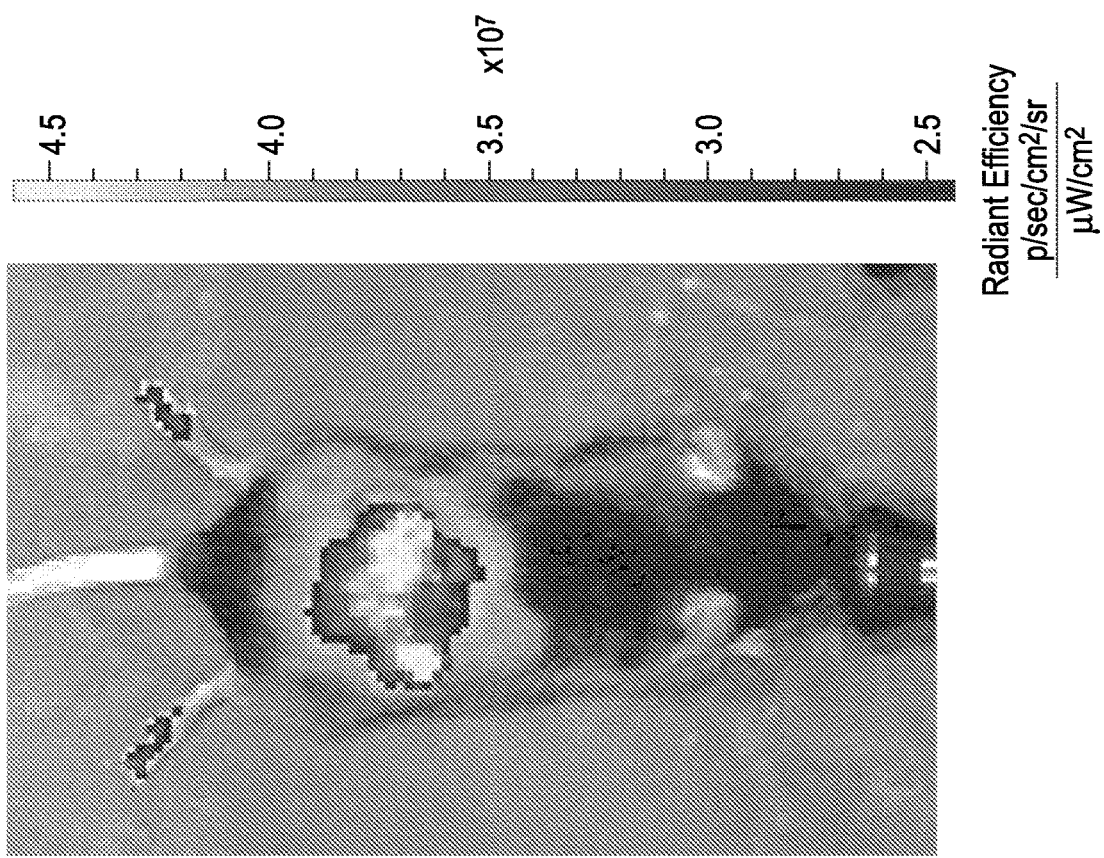
FIG. 9 depicts one of 10 mice experiments in accordance with various embodiments. Ten mice (C57BL/6 mice) were implanted with breast cancer cells (E0771) to develop breast cancer tumor xenograph model. The tumors were allowed to grow for 4 weeks before the mice were injected with 30 ul of peptide (2 nMoles). The animals were imaged using mouse fluorescence imaging after 1, 2, 3, 4, 6 hr. Notice that within 6 hr, intense fluorescence is already observed within the implanted breast cancer tumors on the rear bilateral flank of the mice.
Figure 11:
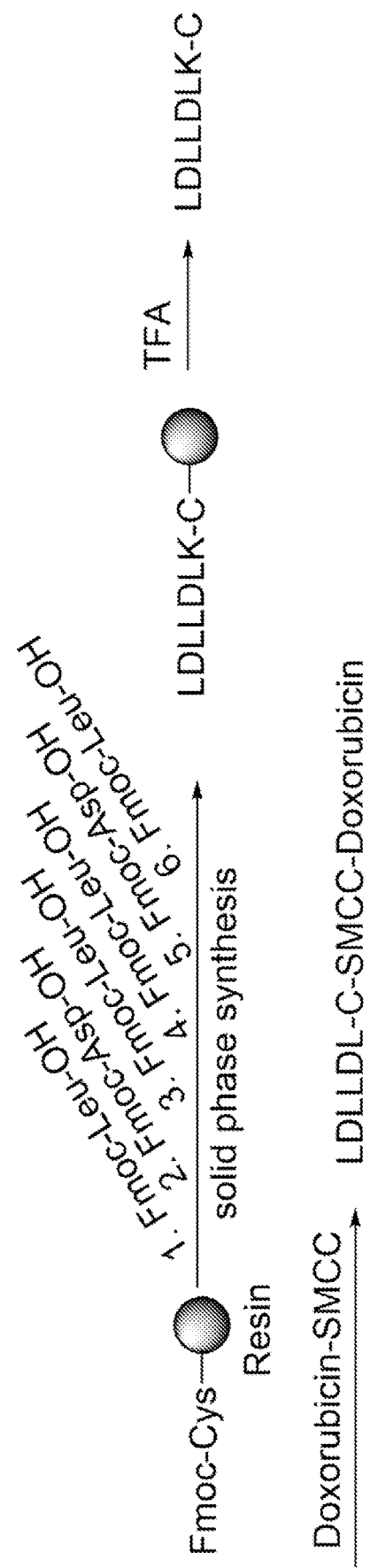
FIG. 11 depicts the synthesis of DOX-LDLLDL (DOX-[SEQ ID NO:1]). The LDLLDL (SEQ ID NO:1) peptide was modified by conjugation with a chemotherapeutic payload for cancer targeted therapy. An additional cysteine residue was incorporated in the construct at the c-terminal end as a handle for the conjugation of doxorubicin. The DOX-LDLLDL (DOX-[SEQ ID NO:1]) was synthesized as shown in Scheme 1. The LDLLDL-C peptide ([SEQ ID NO:1]-C) was synthesized by the solid-phase method via Fmoc strategy, using 2-(1H-benzotriazole-1-yl)-1,1,3,3-tetramethyluronium hexafluorophosphate (HBTU) as the coupling agent on a CS136XT automated peptide synthesizer. After peptide sequence was assembled on Wang Resin, the product was cleaved from the solid support. The resulting crude peptide LDLLDL-C([SEQ ID NO:1]-C) was purified by RP-HPLC. The doxorubicin was conjugated to the peptide at cysteine thiol group via maleimide-thiol coupling through a SMCC linker. The final product, LDLLDL-C-SMCC-doxorubicin ([SEQ ID NO:1]-C-SMCC-DOX ("DOX-LDLLDL" (DOX-[SEQ ID NO:1]) was purified by preparative RP-HPLC.
Figure 12:
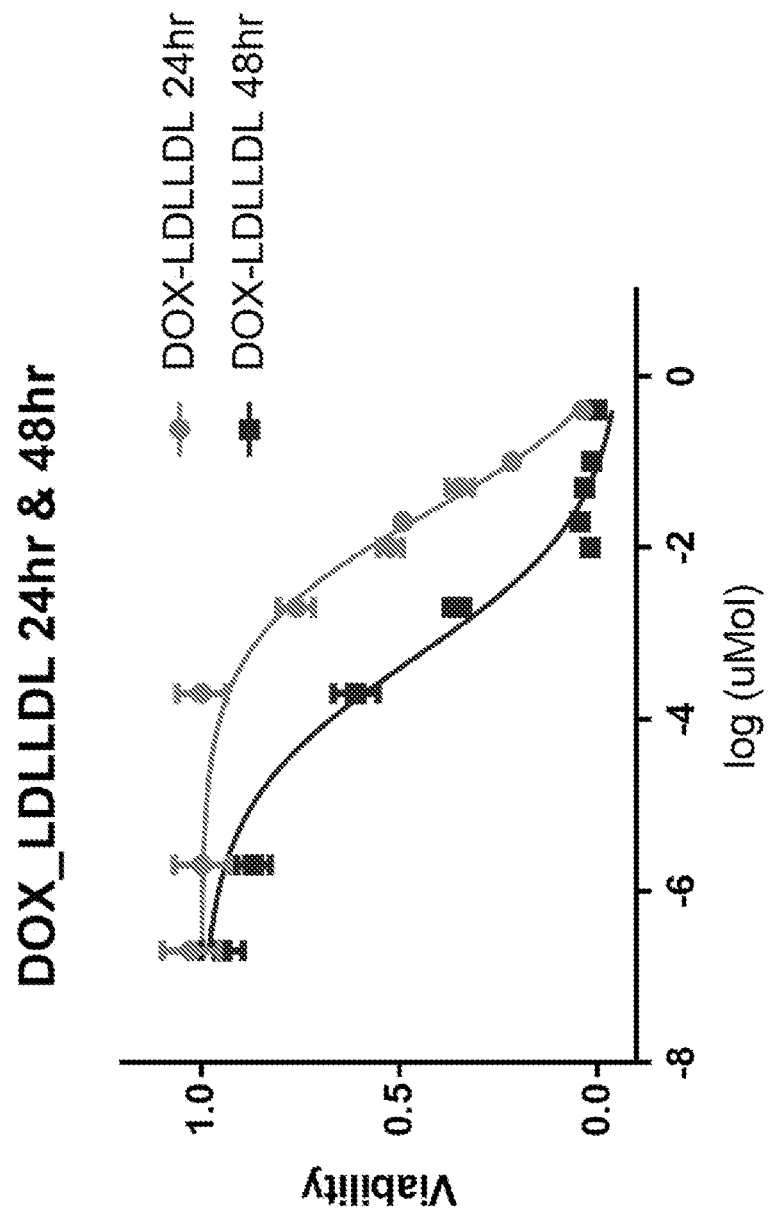
FIG. 12 depicts cell viability of DOX-LDLLDL (DOX-[SEQ ID NO:1]). The 4T1 cells ($5 \times 10^4$ cells/ml) growing in flasks were harvested by treating with 0.2% (w/v) trypsin-0.1% (w/v) EDTA solution. The cells in RPMI 1640 completed medium (200 μL) were seeded in a 96-well plate ($1 \times 10^4$ cells/well) and incubated for one day. The DOX-LDLLDL (DOX-[SEQ ID NO:1]) was prepare with various concentrations (from 0.05 to 10-7 μMol/ml) for dose-dependent cytotoxicity test. The pH of the culture medium was adjusted to pH 6.8 with 0.1 N HCl After 24 h and 48 h incubation, the cells were washed three times with PBS (pH 7.4). The absorbance of each well was read with a microplate reader (Model 680 microplate reader, Bio-Rad) using a test wavelength of 450 nm. Figure shows the results of the cell viability of DOX-LDLLDL (DOX-[SEQ ID NO:1]) after the treatment of 24 h and 48 h.

Characterization of the In Vivo Imaging Profile of $^{64}$Cu-LDLLDL ($^{64}$Cu-[SEQ ID NO:1]) and its Tumor Specific Targeting in a Human Breast Cancer Xenograft Model Without being bound to any particular theory, the inventors believe that ANXA1 is associated with tumorigenesis and progression, and the synthesized peptide imaging probe can be used as a surrogate for monitoring the tumor expression with ANXAL. To characterize target specificity, the inventors developed the breast cancer xenograft model with ANXA1 overexpression as well as an ANXA1-knockdown model using a shRNA lentiviral vector technique. The xenograft breast cancer model with ANXA1 overexpression has a significantly high uptake of FPR peptide LDLLDL-$^{64}$Cu ([SEQ ID NO:1]-$^{64}$Cu) in PET image studies. While the mice with knockdown of ANXA1 have a significantly reduce cellular proliferation and invasion and a reduced uptake of the peptide. The inventors assess the pharmacokinetic profile and tumor specific targeting potency of the new imaging probe, and its effectiveness in evaluation of tumorigenesis and progression of aggressive breast cancer. See FIG. 8 for experimental design.

Methods

Breast cancer xenograft model: In vitro studies described above identified the expression of ANXA1/FPR1 for all tested cells. The inventors then select the cell line with highest ANXA1 expression (e.g. MDA-MB-231) to develop the breast cancer xenograft. Female athymic nude mice are subcutaneously inoculated in the right flank with $1\times10^7$ cells. Following introduction into nude mice, subcutaneously palpable tumors appear in 48-72 hours. Body weight and tumor volume is measured weekly. Once the tumor volume surpasses 0.5 cm$^3$ or the tumor(s) have grown to 100-400 mg, PET studies are performed on a microPET (Concorde Microsystems, Knoxville, Tenn.).

Blood clearance and biodistribution: i) Blood clearance: After anesthesia (isoflurane 2-3%), 2 groups of 5 mice each are injected with radiolabeled LDLLDL-$^{64}$Cu ([SEQ ID NO:1]-$^{64}$Cu) (~5 µCi) via tail vein. Retro-orbital blood samples (25 µL) are collected at various time points such as 5, 15, 30, 60, 120, 240 min and 24 h after injection and radioactivity of all samples are counted in a gamma counter (Perkin-Elmer). Results are normalized and plotted against injection time, followed by non-linear regression analysis to obtain half-life time in blood (GraphPad Prism). Mice are sacrificed immediately after the last blood sampling. Tumors and organs (such as the heart, liver, lung, kidney, small intestine, stomach, bone, muscle, spleen and skin) are harvested and counted for radioactivity using a gamma counter. ii) Biodistribution: The mice are administered LDLLDL-$^{64}$Cu ([SEQ ID NO:1]-$^{64}$Cu) (100 µCi per animal) via tail vain. At 1 h, 2 h, 4 h, 24 h after injection, mice are scanned by small-animal PET followed by tissue radioactivity assay. Specifically, animals are sacrificed after each scan, after which the tissues and organs of interest are collected and weighed, and radioactivity is counted with a gamma counter. Uptake of radioactivity in the tumor and normal tissues and organs is expressed as a percentage of the injected radioactive dose per gram (% ID/g). Whole-blood % ID or % ID/g is determined assuming the blood accounted for 6.5% of the body weight of the mouse.

Construction of ANXA1 knockdown model: The inventors stably transduce ANXA1 shRNA-expressing lentiviral constructs into the selected cell line with highest ANXA1 expression (e.g. MDA-MB-231). Pooled ANXA1-knockdown (ANXA1-KD) clones are used for subsequent experiments. A scrambled (SCR) shRNA is prepared in the same method, and used as a control (ANXA1-SCR).

Assessment of cellular proliferation by knockdown of ANXA1: To assess cellular LDLLDL-$^{64}$Cu ([SEQ ID NO:1]-$^{64}$Cu) uptake mediated by ANXA1, the ANXA1-KD and ANXA1-SCR cells are seeded into a 24-well plate ($1\times10^5$ cells/well) and cultured under a serum starvation condition for 24 h. After incubation of the cells with LDLLDL-$^{64}$Cu ([SEQ ID NO:1]-Cu) (2 µCi/well) at 37° C. for 1 h, the cells are harvested and washed 3 times with cold PBS. The radioactivity of the cells is counted with a gamma counter. A cell proliferation assay is conducted using a CCK-8 Cell Proliferation Assay kit (Dojindo) in triplicate for each point and repeated 3 times.

Evaluation of tumor uptake in ANXA1 knockdown xenograft model: The inventors evaluate the effects of ANXA1 in regulating tumorigenesis and progression using the ANXA1-KD/control breast cancer xenograft model. Specifically, female athymic nude mice are randomly assigned into two groups with knockdown (ANXA1-KD) and control (ANXA1-SCR) cells. Animals are injected with $1\times10^7$ cells subcutaneously in the right flank. Tumor growth and/or progression of the disease is monitored up to 8 weeks after cell inoculation. Using PET/CT imaging, the inventors determine whether there is a significant reduction of LDLLDL-$^{64}$Cu ([SEQ ID NO:1]-$^{64}$Cu) uptake in ANXA1 knockdown tumors, as compared with the uptake of the tumors without knockdown. After the tumor volume surpasses 0.5 cm$^3$, the mice are administered LDLLDL-$^{64}$Cu ([SEQ ID NO:1]-$^{64}$Cu) (100 µCi per animal) via tail vain. At 1 h, 2 h, 4 h, 24 h after injection, the $^{64}$Cu radioactivity of the ANXA1-KD tumors is determined by PET quantification, which is compared to the $^{64}$Cu radioactivity of the control (ANXA1-SCR) tumors. On completion of PET/CT at 24 h after injection, a tissue radioactivity assay is performed, and tissue radioactivity is calculated and expressed as decay-corrected percentage injected dose per gram of tissue (% ID/g). The tumor radioactivity and size are compared between ANXA1-KD tumor and ANXA1-SCR tumor. The inventors assess whether the knockdown of ANXA1 is associated with tumor growth inhibition as well as tumor uptake reduction.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

The invention claimed is:

1. A theranostic peptide agent, comprising:
   a multimodal peptide ligand imaging agent
   a cancer therapeutic agent; and
   optionally, a linker that binds the multimodal peptide ligand imaging agent and the cancer therapeutic agent,
   wherein the multimodal peptide ligand imaging agent comprises:
   a peptide ligand capable of selectively binding to formyl peptide receptor 1 (FPR1);
   an imaging moiety; and
   optionally, a linker that binds the peptide ligand and imaging moiety,
   wherein the peptide ligand comprises the sequence as set forth in SEQ ID NO:1.

2. The theranostic peptide agent of claim 1, wherein the multimodal peptide ligand imaging agent comprises the linker that binds the peptide ligand and imaging moiety.

3. The theranostic peptide agent of claim 1, wherein the peptide ligand consists of SEQ ID NO: 1.

4. The theranostic peptide agent of claim 1, wherein the imaging moiety is a nuclear imaging radioisotope, a magnetic resonance imaging (MRI) imaging probe, or optical imaging fluorophore.

5. The theranostic peptide agent of claim 1, comprising: the linker that binds the multimodal peptide ligand imaging agent and the cancer therapeutic agent.

6. The theranostic peptide agent of claim 1, further comprising an anti-inflammatory agent.

7. The theranostic peptide agent of claim 1, wherein the cancer therapeutic agent comprises a chemotherapy drug.

8. The theranostic peptide agent of claim 7, wherein the chemotherapy drug comprises Platinum agents, Bevacizumab, Docetaxel, Camptothecin, Chlorin E6, Oxaliplatin, Carmustine, Cyclophosphamide, Vincristine, Ixabepilone, Eribulin, Vinorelbine, Vinblastine, Irinotecan, Topotecan, Etoposide, Paclitaxel, Doxorubicin, Lomustine, Everolimus, Temozolomide, Taxotere, Pemetrexed, Cabazitaxel, Estramustine, Capecitabine, Gemcitabine, and/or Mitoxantrone.

9. The theranostic peptide agent of claim 8, wherein the Platinum agents comprise cisplatin and carboplatin.

10. The theranostic peptide agent of claim 9, wherein the chemotherapy drug is cisplatin, Docetaxel, Camptothecin and/or Chlorin E6.

11. A method, comprising:
    administering the theranostic peptide agent of claim 6 to a subject in need thereof;
    assessing the subject by imaging and detecting the multimodal peptide ligand imaging agent; and
    diagnosing the subject with cancer and optionally, inflammation when the multimodal peptide ligand imaging agent is detected.

12. The method of claim 11, wherein the imaging moiety of the multimodal peptide ligand imaging agent detects targeted tissues and/or cells, and wherein the targeted tissues and/or cells comprise tumor and/or immune-associated tumor cells and optionally, inflammatory regions.

13. The method of claim 12, further comprising visualizing the targeted tissues and/or cells using imaging methods.

14. The method of claim 11, further comprising staging the cancer and optionally, inflammation in the subject using the multimodal peptide ligand imaging agent.

15. A method, comprising:
    administering the cancer theranostic peptide agent of claim 1 to a subject with cancer and optionally, inflammation to treat the subject,
    wherein the cancer is an Annexin 1 (ANXA1)-expressing cancer or a formyl peptide receptor 1 (FPR1) expressing cancer.

16. The method of claim 15, further comprising identifying targeted tissues and/or cells by detecting the imaging moiety of the multimodal peptide ligand imaging agent.

17. The method of claim 16, wherein the targeted tissues and/or cells comprise tumor and/or immune-associated tumor cells and optionally, inflammatory regions.

18. The method of claim 16, further comprising visualizing the targeted tissues and/or cells using imaging methods.

19. The method of claim 15, further comprising monitoring a therapeutic response by detecting the imaging moiety of the multimodal peptide ligand imaging agent.

20. The method of claim 19, further comprising monitoring infiltration of tumor-associated macrophages and neutrophils.

* * * * *

SEQUENCE LISTING

<160> NUMBER OF SEQ ID NOS: 1

<210> SEQ ID NO 1
<211> LENGTH: 6
<212> TYPE: PRT

```
<213> ORGANISM: Artificial Sequence
<220> FEATURE:
<223> OTHER INFORMATION: synthetic construct

<400> SEQUENCE: 1

Leu Asp Leu Leu Asp Leu
1               5
```